United States Patent [19]

Hindley

[11] Patent Number: 5,260,445

[45] Date of Patent: Nov. 9, 1993

[54] 2,4-THIAZOLIDINEDIONES

[75] Inventor: Richard M. Hindley, Epsom, England

[73] Assignee: Beecham Group p.l.c., Brentford, United Kingdom

[21] Appl. No.: 798,744

[22] Filed: Nov. 27, 1991

Related U.S. Application Data

[60] Division of Ser. No. 641,474, Jan. 15, 1991, Pat. No. 5,232,925, which is a continuation-in-part of Ser. No. 457,272, Dec. 27, 1989, Pat. No. 5,002,953, which is a continuation-in-part of Ser. No. 238,764, Aug. 30, 1988, abandoned.

[30] Foreign Application Priority Data

Sep. 4, 1987 [GB] United Kingdom ............ 8720825
Nov. 30, 1987 [GB] United Kingdom ............ 8727987
Feb. 4, 1988 [GB] United Kingdom ............ 8802454

[51] Int. Cl.$^5$ ............................................. C07D 277/34
[52] U.S. Cl. ..................................................... 548/183
[58] Field of Search ........................................ 548/183

[56] References Cited

U.S. PATENT DOCUMENTS 4,376,777 3/1983 Kawamatsu ...................... 548/183
4,725,610 2/1985 Meguro .............................. 514/369

FOREIGN PATENT DOCUMENTS 2082584 3/1982 United Kingdom .

Primary Examiner—Robert Gerstl
Attorney, Agent, or Firm—Hopgood, Calimafde, Kalil, Blaustein & Judlowe

[57] ABSTRACT

Compounds of formula (I):

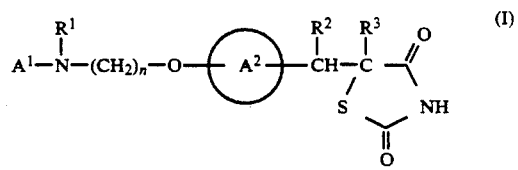

or a tautomeric form thereof, or a pharmaceutically acceptable salt thereof, or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$R^2$ and $R^3$ each represent hydrogen, or $R^2$ and $R^3$ together represent a bond;

$A^2$ represents a benzene ring having in total up to five substituents; and n represents an integer in the range of from 2 to 6; pharmaceutical compositions containing such compounds and the use of such compounds and compositions in medicine.

1 Claim, No Drawings

2,4-THIAZOLIDINEDIONES

This application is a division of copending application Ser. No. 641,474, filed Jan. 15, 1991, U.S. Pat. No. 5,233,925 which is based on U.S. Ser. No. 457,272, filed Dec. 27, 1989, now U.S. Pat. No. 5,002,953, which in turn is a Continuous-In-Part of U.S. Ser. No. 238,764, filed Aug. 30, 1988, now abandoned.

This invention relates to certain substituted thiazolidinedione derivatives, to a process for preparing such compounds, to pharmaceutical compositions containing such compounds and to the use of such compounds and compositions in medicine.

European Patent Applications, Publication Numbers 0008203, 0139421, 0155845, 0177353, 0193256, 0207581 and 0208420 relate to thiazolidinedione derivatives which are disclosed as having hypoglycaemic and hypolipidaemic activity. Chem. Pharm. Bull 30 (10) 3580–3600 also relates to certain thiazolidinedione derivatives having hypoglycaemic and hypolipidaemic activities.

It has now surprisingly been discovered that certain novel substituted-thiazolidinedione derivatives show improved blood-glucose lowering activity and are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia, hypertension, cardiovascular disease and certain eating disorders.

Accordingly, the present invention provides a compound of formula (I):

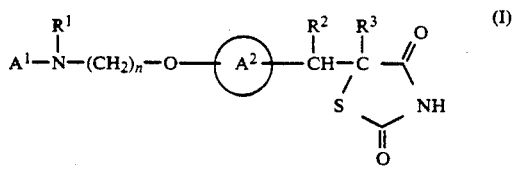

or a tautomeric form thereof and/or a pharmaceutically acceptable salt thereof, and/or a pharmaceutically acceptable solvate thereof, wherein:
$A^1$ represents a substituted or unsubstituted aromatic heterocyclyl group;
$R^1$ represents a hydrogen atom, an alkyl group, an acyl group, an aralkyl group, wherein the aryl moiety may be substituted or unsubstituted, or a substituted or unsubstituted aryl group;
$R^2$ and $R^3$ each represent hydrogen, or $R^2$ and $R^3$ together represent a bond;
$A^2$ represents a benzene ring having in total up to five substituents; and
n represents an integer in the range of from 2 to 6.

Suitable aromatic heterocyclyl groups include substituted or unsubstituted, single or fused ring aromatic heterocyclyl groups comprising up to 4 hetero atoms in each ring selected from oxygen, sulphur or nitrogen.

Favoured aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2 or 3 heteroatoms, especially 1 or 2, selected from oxygen, sulphur or nitrogen.

Suitable values for $A^1$ when it represents a 5- membered aromatic heterocyclyl group include thiazolyl and oxazolyl, especially oxazolyl.

Suitable values for $A^1$ when it represents a 6- membered aromatic heterocyclyl group include pyridyl or pyrimidinyl.

Suitably $R^2$ and $R^3$ each represent hydrogen.

Preferably, $A^1$ represents a moiety of formula (a), (b) or (c):

(a)

(b)

(c)

wherein:
$R^4$ and $R^5$ each independently represents a hydrogen atom, an alkyl group or a substituted or unsubstituted aryl group or when $R^4$ and $R^5$ are each attached to adjacent carbon atoms, then $R^4$ and $R^5$ together with the carbon atoms to which they are attached form a benzene ring wherein each carbon atom represented by $R^4$ and $R^5$ together may be substituted or unsubstituted; and in the moiety of formula (a) X represents oxygen or sulphur.

Aptly, $A^1$ represents a moiety of the abovedefined formula (a).

Aptly, $A^1$ represents a moiety of the abovedefined formula (b).

Aptly, $A^1$ represents a moiety of the abovedefined formula (c).

In one favoured aspect $R^4$ and $R^5$ together represent a moiety of formula (d):

(d)

wherein $R^6$ and $R^7$ each independently represent hydrogen, halogen, substituted or unsubstituted alkyl or alkoxy.

Suitably, $R^6$ and $R^7$ each independently represent hydrogen, halogen, alkyl or alkoxy.

Favourably, $R^6$ represents hydrogen. Favourably, $R^7$ represents hydrogen.

Preferably, $R^6$ and $R^7$ both represent hydrogen.

In a further favoured aspect $R^4$ and $R^5$ each independently represent hydrogen, alkyl or a substituted or unsubstituted phenyl group and more favourably, $R^4$ and $R^5$ each independently represent hydrogen, alkyl or phenyl.

Preferably, for the moiety of formula (a), $R^4$ and $R^5$ together represent the moiety of formula (d).

Preferably, for the moieties of formula (b) or (c), $R^4$ and $R^5$ both represent hydrogen.

It will be appreciated that the five substituents of $A^2$ include three optional substituents. Suitable optional substituents for the moiety $A^2$ include halogen, substituted or unsubstituted alkyl or alkoxy.

Favourably, $A^2$ represents a moiety of formula (e):

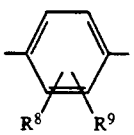

(e)

wherein $R^8$ and $R^9$ each independently represent hydrogen, halogen, substituted or unsubstituted alkyl or alkoxy.

Suitably, $R^8$ and $R^9$ each independently represent hydrogen, halogen, alkyl or alkoxy. Preferably, $R^8$ and $R^9$ each represent hydrogen.

Favourably, X represents oxygen. Favourably, X represents sulphur.

In one preferred aspect the present invention provides a class of compounds, which fall wholly within the scope of formula (I), of formula (II):

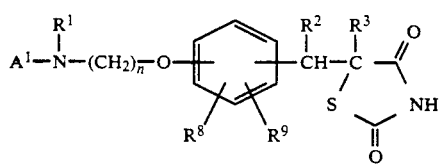

(II)

or a tautomeric form thereof, and/or a pharmaceutically acceptable salt thereof and/or a pharmaceutically acceptable solvate thereof, wherein $A^1$, $R^1$, $R^2$, $R^3$, and n are as defined in relation to formula (I) and $R^8$ and $R^9$ are as defined in relation to formula (e).

Suitably, n represents an integer 2, 3 or 4, notably 2 or 3 and especially 2.

Suitably, $R^1$ represents hydrogen, alkyl, acyl, especially acetyl, or benzyl.

When $R^1$ represents an alkyl group, examples of such alkyl groups include methyl and isopropyl. Preferably, $R^1$ represents a methyl group.

As indicated above a compound of formula (I) may exist in one of several tautomeric forms, all of which are encompassed by the present invention. It will be appreciated that the present invention encompasses all of the isomeric forms of the compounds of formula (I) and the pharmaceutically acceptable salts thereof, including any stereoisomeric forms thereof, whether as individual isomers or as mixtures of isomers.

Suitable substituents for any heterocyclyl group include up to 4 substituents selected from the group consisting of: alkyl, alkoxy, aryl and halogen or any two substituents on adjacent carbon atoms, together with the carbon atoms to which they are attached, may form an aryl group, preferably a benzene ring, and wherein the carbon atoms of the aryl group represented by the said two substituents may themselves be substituted or unsubstituted.

When used herein the term 'aryl' includes phenyl and naphthyl optionally substituted with up to five, preferably up to three, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

When used herein the term 'halogen' refers to fluorine, chlorine, bromine and iodine; preferably chlorine.

When used herein the terms 'alkyl' and 'alkoxy' relate to groups having straight or branched carbon chains, containing up to 12 carbon atoms.

When used herein the term 'acyl' includes alkylcarbonyl groups

Suitable alkyl groups are $C_{1-12}$ alkyl groups, especially $C_{1-6}$ alkyl groups e.g. methyl, ethyl, n-propyl, iso-propyl, n-butyl, isobutyl or tert-butyl groups Suitable substituents for any alkyl group include those indicated above in relation to the term "aryl".

Suitable pharmaceutically acceptable salts include salts of the thiazolidinedione moiety, and, where appropriate, salts of carboxy groups.

Suitable pharmaceutically acceptable salts of the thiazolidinedione moiety include metal salts especially alkali metal salts such as the lithium, sodium and potassium salts.

Suitable pharmaceutically acceptable salts of carboxy groups include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable pharmaceutically acceptable solvates include hydrates.

In a further aspect the present invention also provides a process for the preparation of a compound of formula (I), or a tautomeric form thereof, and/or a pharmaceutically acceptable salt thereof, and/or a pharmaceutically acceptable solvate thereof, which process comprises reacting a compound of formula (III):

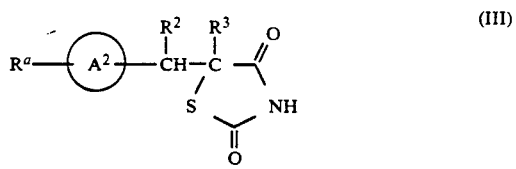

(III)

wherein $R^2$, $R^3$ and $A^2$ are as defined in relation to formula (I), and $R^1$ is a moiety convertible to a moiety of formula (f):

(f)

wherein $R^1$, $A^1$, and n are as defined in relation to formula (I), with an appropriate reagent capable of converting $R^1$ to the said moiety (f) and thereafter, if required, carrying out one or more of the following optional steps:

(i) converting a compound of formula (I) to a further compound of formula (I);

(ii) preparing a pharmaceutically acceptable salt of the compound of formula (I) and/or a pharmaceutically acceptable solvate thereof.

Suitably, $R^a$ represents $R^1HN-(CH_2)_n-O-$ wherein $R^1$ and n are as defined in relation to formula (I).

Suitably, when $R^a$ is $R^1HN-(CH_2)_n-O-$, an appropriate reagent capable of converting $R^a$ to a moiety (f) is a compound of formula (IV):

$$A^1-R^x \quad \text{(IV)}$$

wherein $A^1$ is as defined in relation to formula (I) and $R^x$ represents a leaving group.

A suitable leaving group Rx includes a halogen atom, preferably a chlorine or bromine atom, or a thioalkyl group for example a thiomethyl group.

The reaction between the compound of formula (III) and the appropriate reagent may be carried out under conditions suitable to the particular compound of formula (III) and the reagent chosen; thus for example the abovementioned reaction between a compound of formula (III) wherein $R^a$ represents $R^1HN-(CH_2)_n-O-$ and the compound of formula (IV), may be carried out in any suitable solvent, for example tetrahydrofuran, at a temperature in the range of between 0° and 60° C.

A compound of formula (III) may be prepared from a compound of formula (V):

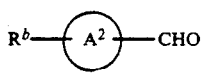
(V)

wherein $A^2$ is as defined in relation to the compound of formula (I) and $R^b$ is a moiety $R^a$, or a moiety convertible to a moiety $R^a$; by reaction of the compound of formula (V) with 2,4-thiazolidinedione; and thereafter if required carrying out one or more of the following optional steps:

(i) reducing a compound of formula (III) wherein $R^2$ and $R^3$ together represent a bond, into a compound of formula (III) wherein $R^2$ and $R^3$ each represent hydrogen;

(ii) converting a moiety $R^b$ to a moiety $R^a$.

The reaction between the compound of formula (V) and 2,4-thiazolidinedione will of course be carried out under conditions suitable to the nature of the compound of formula (V), in general the reaction being carried out in a solvent such as toluene, suitably at an elevated temperature such as the reflux temperature of the solvent and preferably in the presence of a suitable catalyst such as piperidinium acetate or benzoate. Favourably, in the reaction between the compound of formula (V) and 2,4-thiazolidinedione, the water produced in the reaction is removed from the reaction mixture, for example by means of a Dean and Stark apparatus.

When $R^a$ represents $R^1HN-(CH_2)_n-O-$, a suitable value for $R^b$ is a hydroxyl group.

The moiety $R^b$ may be converted to the moiety $R^a$ by any suitable means, for example when $R^b$ represents a hydroxyl group and $R^a$ represents $R^1HN(CH_2)_n-O-$ the appropriate conversion may be carried out by coupling a compound of formula (VA):

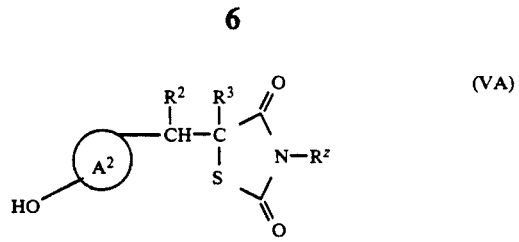

wherein $R^2$, $R^3$ and $A^2$ are as defined in relation to formula (I) and $R^z$ is hydrogen or a nitrogen protecting group, with a compound of formula (VI):

$$R^1NR^x(CH_2)_n-OH \quad \text{(VI)}$$

wherein $R^1$ and n are as defined in relation to formula (I) and $R^x$ is hydrogen or a nitrogen protecting group, in the presence of a suitable coupling agent; and thereafter, if required, carrying out one or more of the following optional steps:

(i) reducing a compound of formula (III) wherein $R^2$ and $R^3$ together represent a bond, to a compound of formula (III) wherein $R^2$ and $R^3$ each represent hydrogen;

(ii) removing any nitrogen protecting group.

A suitable coupling agent for the coupling reaction between the compound of formula (VA) and (VI) is provided by diethylazodicarboxylate and triphenylphosphine. The coupling reaction may be carried out in any suitable solvent at a low to medium temperature, for example in tetrahydrofuran at a temperature in the range of between 0° and 60° C.

One example of the preparation of a compound of formula (VA) is that wherein a compound falling within formula (V) of particular formula (VII):

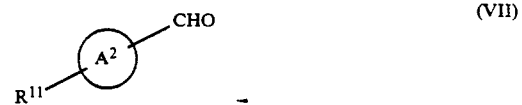

wherein $A^2$ is as defined in relation to formula (I), and $R^{11}$ represents a hydroxyl group or a protected hydroxyl group, is reacted with 2,4-thiazolidinedione; and thereafter if required removing any protecting group.

Preferably, $R^{11}$ represents a benzyloxy group.

Suitable conditions for the reaction between a compound of formula (VII) and 2,4-thiazolidinedione are those defined above in relation to the reaction between the compounds of formula (V) and 2,4-thiazolidinedione.

The compounds of formula (IV), (VI) and (VII) are either known compounds or are prepared using methods analogous to those used to prepare known compounds.

Suitable protecting groups in any of the abovementioned reactions are those used conventionally in the art. Thus, for example, a suitable nitrogen protecting group is a benzyl group or a benzyloxycarbonyl group and a suitable hydroxyl protecting group is a benzyl group.

The methods of formation and removal of such protecting groups are those conventional methods appropriate to the molecule being protected. Thus for example when $R^{11}$ represents a benzyloxy group such group may be prepared by treatment of the appropriate compound of formula (VII), wherein $R^{11}$ is a hydroxyl group with a benzyl halide, such as benzyl bromide, and thereafter when required the benzyl group may be conveniently removed using a mild ether cleavage reagent such as trimethylsilyliodide.

A compound of formula (I), or a tautomeric form thereof, and/or a pharmaceutically acceptable salt thereof and/or a pharmaceutically acceptable solvate thereof, may also be prepared by reacting a compound of formula (VIII):

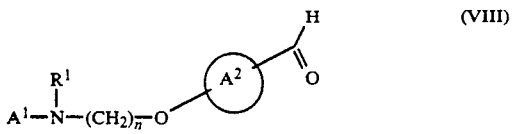

wherein $R^1$, $A^1$, $A^2$, and n are as defined in relation to formula (I) with 2,4-thiazolidinedione; and thereafter if required carrying out one or more of the following optional steps:
(i) converting a compound of formula (I) into a further compound of formula (I);
(ii) preparing a pharmaceutically acceptable salt of a compound of formula (I) and/or a pharmaceutically acceptable solvate thereof.

The reaction between a compound of formula (VIII) and 2,4-thiazolidinedione may suitably be carried out under analogous conditions to those used in the reaction between a compound of formula (V) and 2,4-thiazolidinedione.

A compound of formula (VIII) may be prepared by reacting a compound of formula (IX):

wherein $A^2$ is as defined in relation to formula (I) and $R^a$ is as defined in relation to formula (III), with an appropriate reagent capable of converting $R^a$ to the above defined moiety (f).

Suitable values for $R^a$ include those described above in relation to the compound of formula (III). Thus $R^a$ may represent $R^1HN-(CH_2)_n-O-$, as defined above, and hence the appropriate compound of formula (IX) may be reacted with a reagent of the abovedefined formula (IV) to provide the required compound of formula (VIII).

Suitable reaction conditions for the reaction of the compound of formula (IX) and the appropriate reagent may include those described above in relation to the preparation of compound (III) with the said appropriate reagent.

Preferably, for the compound of formula (IX), $R^a$ represents a leaving group, especially a fluorine atom. When $R^a$ represents a leaving group, preferably a fluorine atom, a particularly appropriate reagent is a compound of formula (X):

wherein $R^1$, $A^2$, and n are as defined in relation to formula (I).

The reaction between the compounds of formulae (IX) and (X) may be carried out under any suitable conditions, (X) may be for example in a solvent such as dimethylformamide or dimethylsulphoxide at an elevated temperature for example in the range of between 100° to 150° C., suitably in the presence of a base such as sodium hydride or potassium carbonate.

In the compound of formula (IX) $R^a$ may also represent a hydroxyl group.

When $R^a$, in the compound of formula (IX), represents a hydroxyl group a particularly appropriate reagent is a compound of the abovedefined formula (X) or a compound of formula (XA):

wherein $A^1$, $R^1$ and n are as defined in relation to formula (X) and $R^y$ represents a tosylate or mesylate group.

The reaction between the compound of formula (IX) wherein $R^a$ is a hydroxyl group and the reagent of the wherein abovedefined formula (X) may suitably be carried out in an aprotic solvent, such as tetrahydrofuran, at low to medium temperature, for example at ambient temperature, and preferably in the presence of a coupling agent such as that provided by triphenylphosphine and diethylazodicarboxylate.

The reaction between the compound of formula (IX), wherein $R^a$ is a hydroxyl group, and the reagent of the abovedefined formula (XA) may be carried out in an aprotic solvent, such as dimethylformamide, at a low to elevated temperature, for example in the range of from 50° C. to 120° C. and preferably in the presence of a base, such as sodium hydride.

The compound of formula (XA) may be prepared from the corresponding compound of formula (X) by reaction with either a tosyl halide or a mesyl halide in a solvent such as pyridine.

The compounds of formula (IX) are known compounds or compounds prepared by methods analogous to those used to prepare known compounds, for example 4-fluorobenzaldehyde and 4-hydroxybenzaldehyde are known commercially available compounds.

The reagent of formula (X) may be prepared by reacting a compound of the hereinabove defined formula (IV), with a compound of the hereinbefore defined formula (VI) and thereafter if required removing any nitrogen protecting group using the appropriate conventional conditions.

The reaction between the compounds of formula (IV) and (VI) may be carried out under any suitable conditions, such as in solvent, for example in an aprotic solvent such as tetrahydrofuran, at a low to medium temperature, for example a temperature in the range of from 0° to 60° C.

Favourably when $R^1$ represents hydrogen the reaction is carried out using the compound of formula (VI) as a solvent at a low to elevated temperature, suitably an elevated temperature such as in the range of between 100° and 170° C.

The abovementioned conversion of a compound of formula (I) into a further compound of formula (I) includes the following conversions:
(a) reducing a compound of formula (I) wherein $R^2$ and $R^3$ together represent a bond, to a compound of formula (I) wherein $R^2$ and $R^3$ each represent hydrogen; and (b) converting one group $R^1$ into another group $R^1$.

The conversion of a compound of formula (I) to a further compound of formula (I) may be carried out by using any appropriate conventional procedure.

A suitable reduction method for the abovementioned conversion (a) includes catalytic reduction or the use of a metal/solvent reducing system.

Suitable catalysts for use in the catalytic reduction are palladium on carbon catalysts, preferably a 10% palladium on charcoal catalyst; the reduction being carried out in a solvent, for example dioxan, suitably at ambient temperature.

Suitable metal/solvent reducing systems include magnesium in methanol.

The abovementioned reduction of a compound of formula (III) wherein $R^2$ and $R^3$ together represent a bond to a compound of formula (III) wherein $R^2$ and $R^3$ each represent hydrogen, may be carried out under analogous conditions to those referred to above in conversion (a) of the compound of formula (I).

In the abovementioned conversion (b), suitable conversions of one group $R^1$ into another group $R^1$ includes converting a group $R^1$ which represents hydrogen into a group $R^1$ which represents an acyl group.

The conversion of a compound of formula (I) wherein $R^1$ represents hydrogen into a compound of formula (I) wherein $R^1$ represents acyl may be carried out using any appropriate conventional acylation procedure, such as by treating an appropriately protected compound of formula (I) with an acylating agent. For example acetic anhydride may be used to prepare the compound of formula (I) wherein $R^1$ is acetyl.

It will be appreciated that in the abovementioned conversions (a) and (b), any reactive group in the compound of formula (I) would be protected, according to conventional chemical practice, where necessary.

Where appropriate the isomeric forms of the compounds of formula (I) and the pharmaceutically acceptable salts thereof may be prepared as individual isomers using conventional chemical procedures.

As mentioned above the compounds of the invention are indicated as having useful therapeutic properties:

The present invention accordingly provides a compound of formula (I), or a tautomeric form thereof and/or a pharmaceutically acceptable salt thereof and/or a pharmaceutically acceptable solvate thereof, for use as an active therapeutic substance.

Thus the present invention provides a compound of formula (I), or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable salt thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable salt thereof and/or a pharmaceutically acceptable solvate thereof for use in the treatment of hypertension, cardiovascular disease and certain eating disorders.

A compound of formula (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a tautomeric form thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the i treatment and/or prophylaxis of hyperglycaemia in a human or non-human mammal which comprises administering an effective, non-toxic, amount of a compound of the general formula (I), or a tautomeric form thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of a compound of formula (I), or a tautomeric form thereof and/or a pharmaceutically acceptable salt thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of the general formula (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 500 mg.

In the treatment and/or prophylaxis of hyperglycaemic non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

The following Procedures and Examples illustrate the invention but do not limit it in any way.

Preparation 1

4-[2-(N-Methyl-N-(2-benzothiazolyl)amino)ethoxy]-benzaldehyde

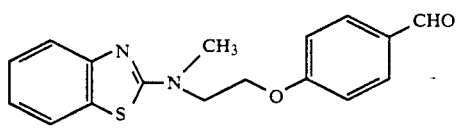

A mixture of 4-fluorobenzaldehyde (1.5g) and 2-[N-methyl-N-(2-benzothiazolyl)amino]ethanol (2.4g) in dimethyl sulphoxide (50 ml) containing anhydrous potassium carbonate (2 g) was stirred at 100° C. for 24 hours. The mixture was cooled to room temperature and added to water (300 ml). The aqueous solution was extracted with diethyl ether (2×300 ml). The organic extracts were washed with brine (1×300 ml), dried (MgSO$_4$), filtered and evaporated to dryness. The title compound was obtained as a waxy solid following chromatography on silica-gel in 1% methanol in dichloromethane.

$^1$H NMR δ (CDCl$_3$)
3.2 (3H, s); 3.8 (2H, t); 4.2 (2H, t);
6.8-7.8 (8H, complex); 9.8 (1H, s).

Preparation 2

2-[N-Methyl-N-(2-benzothiazolyl)amino]ethanol

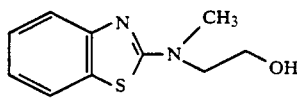

A mixture of 2-chlorobenzothiazole (8.5 g) and 2-methylaminoethanol (20 ml) was heated at 120° C. under pressure in a sealed, glass lined, stainless steel reaction vessel for 18 hours. After cooling, the oil was added to water (100 ml), extracted with dichloromethane (2×100 ml), the organic extracts were dried (MgSO$_4$), filtered and evaporated to dryness. Chromatography of the residual oil on silica-gel in 2½% methanol in dichloromethane gave the title compound which was used in Preparation 1 without further purification.

$^1$H NMR δ (CDCl$_3$)
3.15 (3H, s); 3.4-4.0 (4H, m); 4.7 (1H, broad s, exchanges with D$_2$O); 6.8-7.6 (4H, complex).

Preparation 3

4-[2-(N-Methyl-N-(2-benzoxazolyl)amino)ethoxy]-benzaldehyde

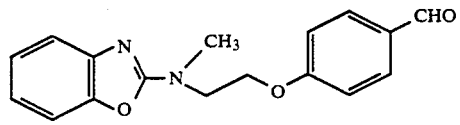

To a solution of 2-[N-methyl-N-(2-benzoxazolyl) amino]ethanol (9.6 g), triphenylphosphine (13.1 g) and 4-hydroxybenzaldehyde (6.1 g) in dry tetrahydrofuran (150 ml) was added dropwise a solution of diethyl azodicarboxylate (9.0 g) in dry tetrahydrofuran (30 ml), under a blanket of nitrogen with stirring at room temperature. The solution was stirred overnight at room temperature following which the solvent was removed under reduced pressure. The residue was dissolved in diethyl ether (300 ml), filtered and the ether solution was washed with dilute sodium hydroxide solution (200 ml), saturated brine (200 ml), dried (MgSO$_4$), filtered and the solvent evaporated. The title compound (mp 97°-98° C.) was obtained after chromatography on silica-gel, eluting with dichloromethane.

$^1$H NMR δ (CDCl$_3$)
3.30 (3H, s); 3.85 (2H, t); 4.30 (2H, t) 6.80-7.85 (8H, complex); 9.85 (1H, s).

Preparation 4

2-[N-Methyl-N-(2-benzoxazolyl)amino]ethanol

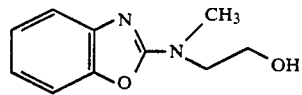

A solution of 2-chlorobenzoxazole (15.4 g) in dry tetrahydrofuran (50 ml) was added dropwise to an ice cooled solution of 2-methylaminoethanol (15.0 g) in dry tetrahydrofuran (100 ml) with stirring and protection from atmospheric moisture. The mixture was stirred at 0° C. for 1 hour, allowed to warm to room temperature and stirred for a further 2 hours. The solvent was removed under reduced pressure, the product was dissolved in ethyl acetate (200 ml) and washed with brine (2×150 ml). The organic layer was dried (MgSO$_4$), filtered and the solvent evaporated. Chromatography of the residue on silica-gel in dichloromethane gave the title compound (mp 62°-3° C.) which was used in Preparation 3 without further purification.

$^1$H NMR δ (CDCl$_3$)
3.12 (3H s); 3.4-4.0 (4H, m); 4.7 (1H, s, exchanges with D$_2$O); 6.8-7.4 (4H, complex).

Preparation 5

4-[2-(N-Methyl-N-(2-pyrimidinyl)amino)ethoxy]-benzaldehyde

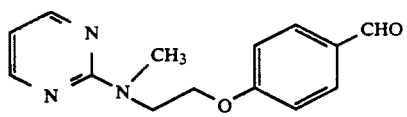

A mixture of 4-fluorobenzaldehyde (12 ml) and 2-[N-methyl-N-(2-pyrimidinyl)amino]ethanol (10.05 g) in dry dimethyl sulphoxide (50 ml) containing anhydrous potassium carbonate (15 g) was stirred at 120° C. for 6 hours. The mixture was cooled to room temperature and added to water (200 ml). The aqueous solution was extracted with ethyl acetate (2×300 ml), the organic extracts washed with brine, dried (MgSO₄) and evaporated. The title compound was obtained as an oil following chromatography on silica-gel in 2% methanol in dichloromethane.

¹H NMR δ (CDCl₃)
3.3 (3H, s); 3.8–4.4 (4H, complex); 6.5 (1H, t); 7.0 (2H, d); 7.8 (2H, d); 8.3 (2H, d); 9.9 (1H, s).

Preparation 6

2-[N-Methyl-N-(2-pyrimidinyl)amino]ethanol

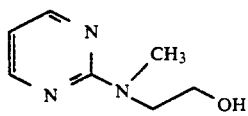

A mixture of 2-chloropyrimidine (10 g) and 2-methylaminoethanol in dry tetrahydrofuran (100 ml) was boiled under reflux for 3 hours. The solution was cooled, water (200 ml) was added, the mixture extracted with dichloromethane, the organic extracts were dried (MgSO₄), filtered and evaporated to dryness. The residual oil was used in Preparation 5 without further purification.

¹H NMR δ (CDCl₃) 3.2 (3H, s); 3.5–3.9 (4H, m); 4.6 (1H, s, exchanges with D₂O); 6.4 (1H, t); 8.2 (2H, d).

Preparation 7

2-[N-Methyl-N-(2-[4,5-dimethylthiazolyl)amino]ethanol

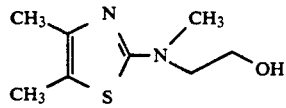

A solution of 2-chloro-4,5-dimethylthiazole (13.2 g) and 2-methylaminoethanol (40 ml) in pyridine (100 ml) was boiled under reflux for 20 hours. After cooling, the oil was added to water (300 ml) and extracted with ethyl acetate (3×200 ml). The organic extracts were washed with brine (2×200 ml), dried (MgSO₄), filtered and evaporated to dryness to leave the title compound which was used in Preparation 14 without further purification.

¹H NMR δ (CDCl₃) 2.15 (3H, s); 2.20 (3H, s); 3.1 (3H, s); 3.4–3.9 (4H, m); 5.25 (1H, broad s, exchanges with D₂O).

Preparation 8

2-[N-Methyl-N-(2-thiazolyl)amino]ethanol

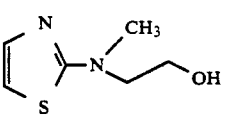

The title compound was prepared as an oil from 2-bromothiazole (15 g) and 2-methylaminoethanol (45 ml) by an analogous procedure to that described in Preparation 7

¹H NMR δ (CDCl₃) 3.1 (3H, s); 3.4–3.9 (4H, m); 4.8 (1H, broad s, exchanges with D₂O); 6.4 (1H, d); 7.0 (1H, d).

Preparation 9

2-[N-Methyl-N-(2-(4-phenylthiazolyl)amino]ethanol

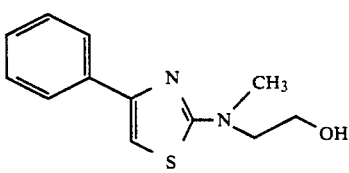

The title compound was prepared as an oil from 2-chloro-4-phenylthiazole (13.5 g) and 2-methylaminoethanol (40 ml) by an analogous procedure to that described in Preparation 7.

¹H NMR δ (CDCl₃) 3.15 (3H, s); 3.6–4.0 (4H, m); 4.6 (1H, broad s, exchanges with D₂O); 6.7 (1H, s); 7.2–7.9 (5H, complex).

Preparation 10

2-[N-Methyl-N-(2-(4-phenyl-5-methylthiazolyl))amino]ethanol

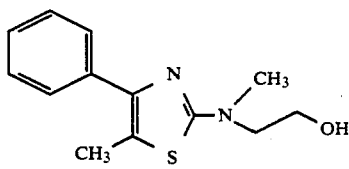

The title compound was prepared as an oil from 2-chloro-4-phenyl-5-methylthiazole (18.9 g) and 2-methylaminoethanol (50 ml) by an analogous procedure to that described in Preparation 7.

¹H NMR δ (CDCl₃) 2.38 (3H, s); 3.0 (3H, s); 3.45–3.85 (4H, m); 5.1 (1H, broad s, exchanges with D₂O); 7.1–7.7 (5H, complex).

Preparation 11

2-[N-Methyl-N-(2-(4-methyl-5-phenylthiazolyl)-)amino]-ethanol

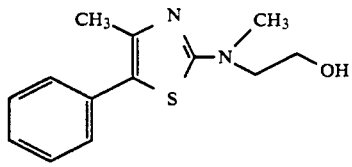

The title compound was prepared as an oil from 2-chloro-4-methyl-5-phenylthiazole (14.8 g) and 2-methylaminoethanol (40 ml) by an analogous procedure to that described in Preparation 7.

$^1$H NMR δ (CDCl$_3$) 2.35 (3H, s); 3.1 (3H, s); 3.5–4.0 (4H, m); 5.1 (1H, broad s, exchanges with D$_2$O); 7.1–7.5 (5H, complex).

Preparation 12

2-[N-Methyl-N-(2-(4-methylthiazolyl))amino]ethanol

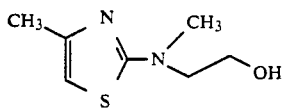

The title compound was prepared, by an analogous procedure to that described in Preparation 7, and was used in the next stage without further purification.

$^1$H NMR δ (CDCl$_3$) 2.25 (3H, s); 3.1 (3H, s); 3.55–3.95 (4H, m); 4.9 (1H, broad s, exchanges with D$_2$O); 6.1 (1H, s).

Preparation 13

2-[N-Methyl-N-[2-(5-phenyloxazolyl)]amino]ethanol

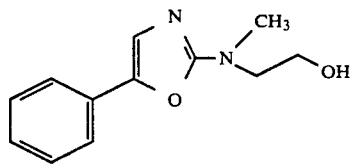

A solution of 2-chloro-5-phenyloxazole (8.3 g) and 2-methylaminoethanol (30 ml) was stirred at 50° C. for 10 minutes. After cooling the oil was added to water (250 ml) and extracted with ethyl acetate (2×150 ml). The organic extracts were washed with brine (2×100 ml), dried (MgSO$_4$), filtered and evaporated to dryness to leave the title compound (m.p. 73°–75° C.).

$^1$H NMR δ (CDCl$_3$) 3.2 (3H, s); 3.6 (2H, t); 3.85 (2H, t); 3.9 (1H, broad s, exchanges with D$_2$O); 7.0 (1H, s); 7.2–7.55 (5H, complex).

Preparation 14

4-[2-(N-Methyl-N-(2-(4,5-dimethylthiazolyl)amino)ethoxy)]benzaldehyde

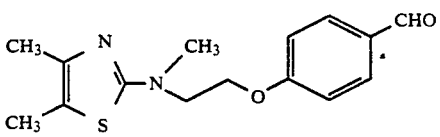

The title compound was prepared from 2-[N-methyl-N-(2-(4,5-dimethylthiazolyl))amino]ethanol (13.2 g) and 4-fluorobenzaldehyde (23.1 g) by an analogous procedure to that described in Preparation 5.

$^1$H NMR δ (CDCl$_3$)

2.15 (3H, s); 2.2 (3H, s); 3.18 (3H, s); 3.8 (2H, t); 4.3 (2H, t); 7.0 (2H, d); 7.8 (2H, d); 10.0 (1H, s).

Preparation 15

4-[2-(N-Methyl-N-(2-thiazolyl)amino)ethoxy]benzaldehyde

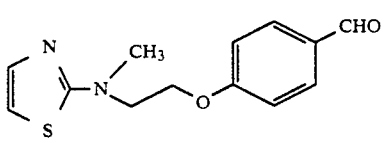

The title compound was prepared from 2-[N-methyl-N-(2-thiazolyl)amino]ethanol (10.7 g) and 4-fluorobenzaldehyde (15.9 g) by an analogous procedure to that described in Preparation 5.

$^1$H NMR δ (CDCl$_3$)

3.15 (3H, s); 3.9 (2H, t); 4.4 (2H, t); 6.5 (1H, d); 7.0 (2H, d); 7.15 (1H, d); 7.8 (2H, d); 9.9 (1H, s).

Preparation 16

4-[2-(N-Methyl-N-(2-(4-phenylthiazolyl)amino)ethoxy)]benzaldehyde

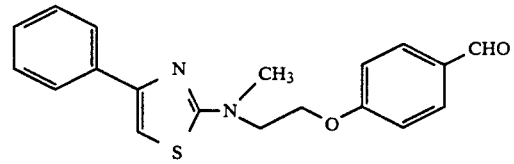

The title compound was prepared from 2-[N-methyl-N-(2-(4-phenylthiazolyl))amino]ethanol (16.1 g) and 4-fluorobenzaldehyde (17.4 g) by an analogous procedure to that described in Preparation 5.

$^1$H NMR δ (CDCl$_3$)

3.2 (3H, s); 3.95 (2H, t); 4.3 (2H, t); 6.7 (1H; s); 6.95–7.9 (9H, complex); 9.9 (1H, s).

Preparation 17

4-[2-(N-Methyl-N-(2-(4-phenyl-5-methylthiazolyl)amino) ethoxy)]benzaldehyde

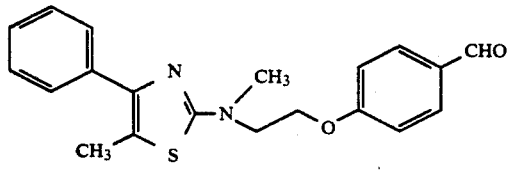

The title compound was prepared from 2-[N-methyl-N-(2-(4-phenyl-5-methylthiazolyl))amino]aminoethanol (13 g) and 4-fluorobenzaldehyde (9.8 g) by a similar procedure to that described in Preparation 5.

¹H NMR δ CDCl₃

2.35 (3H, s); 3.1 (3H, s); 3.8 (2H, t); 4.2 (2H, t); 6.85-7.8 (9H, complex); 9.85 (1H, s).

Preparation 18

4-[2-(N-Methyl-N-(2-(4-methyl-5-phenyl-thiazolyl)amino) ethoxy)]benzaldehyde

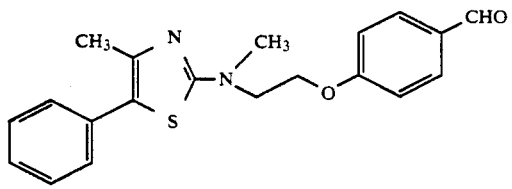

The title compound was prepared from 2-[N-methyl-N-(2-(4-methyl-5-phenylthiazolyl))amino]ethanol (13 g) and 4-fluorobenzaldehyde (13 g) by an analogous procedure to that described in Preparation 5.

¹H NMR δ (CDCl₃)

2.36 (3H, s); 3.2 (3H, s); 3.9 (2H, t); 4.35 (2H, t); 7.05 (2H, d); 7.2-7.5 (5H, complex); 7.85 (2H, d); 9.95 (1H, s).

Preparation 19

4-[2-(N-Methyl-N-(2-(4-methylthiazolyl))amino)ethoxy] benzaldehyde

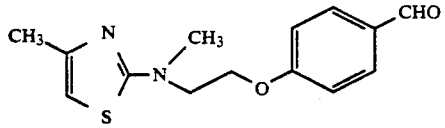

The title compound was prepared from 2-[N-methyl-N-(2-(4-methylthiazolyl))amino]ethanol (12 g) and 4-fluorobenzaldehyde (14.3 g) by an analogous procedure to that described in Preparation 5.

¹H NMR 4 (CDCl₃)

2.25 (3H, s); 3.2 (3H, s); 3.9(2H, t); 4.3 (2H, t); 6.1 (1H, s); 7.05 (2H, d); 7.85 (2H, d); 9.95 (1H, s).

Preparation 20

4-[2-(N-Methyl-N-[2-(5-phenyloxazolyl)]amino)ethoxy] benzaldehyde

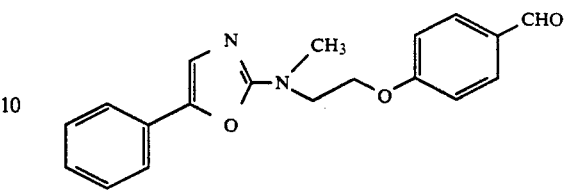

The title compound was prepared from 2-[N-methyl-N-(2-(5-phenyloxazolyl))amino]ethanol (9.3 g) and 4-fluorobenzaldehyde (7.9 g) by an analogous procedure to that described in Preparation 5.

¹H NMR δ (CDCl₃)

3.25 (3H, s); 3.85 (2H, t); 4.3 (2H, t); 6.95-7.6 (8H, complex); 7.8 (2H, d); 9.9 (1H, s).

Preparation 21

2-[N-Methyl-N-[2-(4,5-dimethyloxazolyl)]amino]ethanol

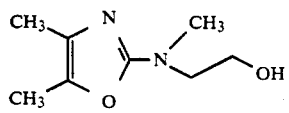

A solution of 2-chloro-4,5-dimethyloxazole (5 g) and 2-methylaminoethanol (15 ml) was stirred at 120° C. for 40 minutes. After cooling the oil was added to water (200 ml) and extracted with dichloromethane (3×200 ml). The organic extracts were washed with brine (2×100 ml), dried (MgSO₄), filtered and evaporated to dryness to leave the title compound as a waxy solid, which was used in Preparation 22 without further purification.

¹H NMR δ (CDCl₃)

1.95 (3H, s); 2.10 (3H, s); 3.05 (3H, s); 3.5 (2H, t); 3.8 (2H, t); 4.4 (1H, broad s, exchanges with D₂O).

Preparation 22

4-[2-(N-Methyl-N-[2-(4,5-dimethyloxazolyl)]amino) ethoxy]benzaldehyde

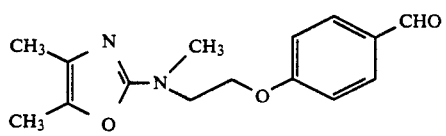

To a stirred solution of 2-[N-methyl-N-[2-(4,5-dimethyloxazolyl)amino]ethanol (2.7 g) in DMF (60 ml), under an atmosphere of nitrogen, was added portionwise sodium hydride (0.7 g; 60% dispersion in oil). After the vigorous reaction had subsided, 4-fluorobenzaldehyde (2.9 g) was added and the reaction mixture was heated to 80° C. for 16 hours. After cooling, the mixture was added to water (400 ml). The aqueous solution was extracted with diethyl ether (3×250 ml). The organic extracts were washed with brine (2×100 ml), dried (MgSO₄), filtered and evaporated to dryness. The title compound was obtained as an oil following chromatography of the residue on silica-gel in 1% methanol in dichloromethane.

¹H NMR δ (CDCl₃) 1.95 (3H, s); 2.15 (3H, s); 3.15 (3H, s); 3.8 (2H, t); 4.25 (2H, t); 7.0 (2H, d); 7.9 (2H, d); 10.0 (1H, s).

Preparation 23

2-(N-(2-Benzoxazolyl)-N-methylamino)ethanol 4-toluene-sulphonyl ester

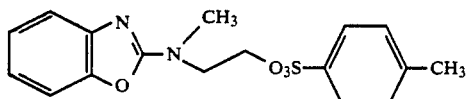

4-Toluenesulphonyl chloride (19.0g) was added portionwise to a solution of N-(2-benzoxazolyl)-N-methylaminoethanol (19.2 g) in dry pyridine (100 ml) at room temperature. The mixture was stirred at room temperature for 3 hours, added to water (500 ml) and extracted with dichloromethane (3×250 ml). The combined extracts were washed with 2M hydrochloric acid (3×250 ml), saturated sodium bicarbonate solution (250 ml) and brine (250 ml), dried (MgSO₄), filtered and evaporated. The title compound was obtained pure following crystallisation from ethanol (m.p. 119°-121° C.).

¹H NMR δ (DMSO-d₆)
2.25 (3H, s); 3.05 (3H, s); 3.75 (2H, t); 4.35 (2H, t); 7.0-7.4 (6H, complex): 7.70 (2H, d).

Preparation 24

2-(N-(2-Benzoxazolyl)-N-methylamino)ethanol methanesulphonyl ester

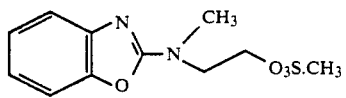

The title compound (m.p. 97°-8° C.) was prepared from N-(2-benzoxazolyl)-N-methylaminoethanol (19.2 g) and methanesulphonyl chloride (11.5 g) by a similar procedure to that used in Preparation 23.

¹H NMR δ (CDCl₃) 2.90 (3H, s); 3.25 (3H, s); 3.7 (2H, t); 4.5 (2H, t); 6.90-7.4 (4H, complex).

Preparation 25

4-[2-(N-Methyl-N-(2-benzoxazolyl)amino)ethoxy]-benzaldehyde

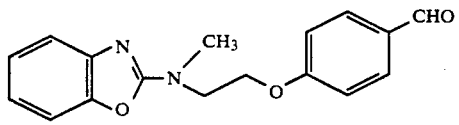

To a solution of 4-hydroxybenzaldehyde (7.32 g) in dry dimethylformamide (100 ml) was added portionwise sodium hydride (60%, 2.4 g) with stirring at room temperature under nitrogen. When gas evolution ceased a solution of 2-(N-methyl-N-(2-benzoxazolyl)amino)ethanol 4-toluenesulphonyl ester (17.3 g) in dry dimethylformamide was added dropwise. The mixture was heated to 80° C. and stirred at this temperature overnight. After cooling, the solution was poured into iced water (1 liter), extracted with ethyl acetate (3×500 ml), and the combined extracts were washed with sodium hydroxide solution (2M; 500 ml) and brine (500 ml), dried (MgSO₄), filtered and evaporated. The title compound (m.p. 96°-98° C.) was obtained pure after crystallisation from ethanol.

¹NMR δ (DMSO-d₆) 3.25 (3H, s); 3.95 (2H, t); 4.40 (2H, t); 6.90-7.40 (6H, complex); 7.85 (2H, d); 9.90 (1H, s).

Preparation 26

4-[2-(N-Methyl-N-(2-benzoxazolyl)amino)ethoxy-benzaldehyde

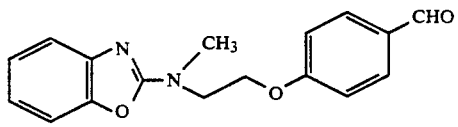

The title compound was prepared from 4-hydroxy benzaldehyde (1.22 g) and 2-(N-methyl-N-(2-benzoxazolyl))-amino)ethanol methanesulphonyl ester (2.7 g) in a similar manner to that described in Preparation 25.

Preparation 27

2-(2-Pyrimidinylamino)ethanol

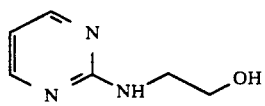

2-Chloropyrimidine (5 g) and ethanolamine (15 ml) were stirred for 2 hours at 140° C. After cooling, the mixture was added to water (200 ml) and continuously extracted with ethyl acetate (500 ml) for 16 hours. The organic extract was dried (MgSO₄), filtered and evaporated to dryness. The title compound was obtained as a solid (m.p. 66° C.), following chromatography on silicagel in 3% methanol in dichloromethane.

¹H NMR δ (CDCl₃) 3.55 (2H, complex); 3.8 (2H, t); 4.3 (1H, broad s, exchanges with D₂O); 6.1 (1H, broad s, exchanges with D₂O); 6.55 (1H, t); 8.3 (2H, d).

Preparation 28

4-[2-(2-Pyrimidinylamino)ethoxy]benzaldehyde

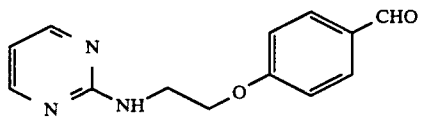

Sodium hydride (1.2 g; 60% dispersion in oil) was added portionwise to a stirred solution of 2-(2-pyrimidinyl amino)ethanol (4 g) in DMF (140 ml) under an atmosphere of nitrogen. After the vigorous reaction had subsided 4-fluorobenzaldehyde (5.35 g) was added and the solution heated to 80° C. for 20 hours. After cooling the mixture was added to water (500 ml) and extracted with diethyl ether (3×300 ml). The organic extracts were washed with brine (2×200 ml), dried (MgSO₄), filtered and evaporated to dryness. Chromatography of the residue on silica gel in 2% methanol in dichloromethane afforded the title compound, which was used in the next stage without further purification.

¹H NMR δ (CDCl₃)

3.8 (2H, complex); 4.2 (2H, t); 5.7 (1H, broad s, exchanges with D₂O); 6.5 (1H, t); 7.0 (2H, d); 7.8 (2H, d); 8.3 (2H, d); 9.9 (1H, s).

Preparation 29

2-(N-(2-Benzothiazolyl)-N-benzylamino)ethanol

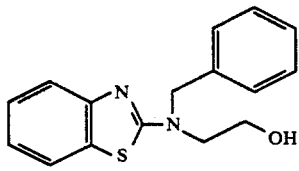

2-Chlorobenzothiazole (13 g) and 2-benzylamino)ethanol (29 g) were heated together in a sealed vessel at 120° C. for 20h . . . After cooling, the reaction mixture was dissolved in ethyl acetate (200 ml) and the solution was washed with saturated aqueous sodium hydrogen carbonate (3×100 ml), water (3×100 ml) and brine (100 ml), dried over anhydrous magnesium sulphate and evaporated to give the title compound (m.p. 95°-96° C.; dichloromethane/hexane).

¹H NMR δ (CDCl₃)
3.8 (4H, m); 4.5 (1H, broad s, exchanges with D₂O); 4.7 (2H, s); 6.9-7.7 (9H, complex).

Preparation 30

4-(2-(N-(2-Benzothiazolyl)-N-benzylamino)ethoxy)-benzaldehyde

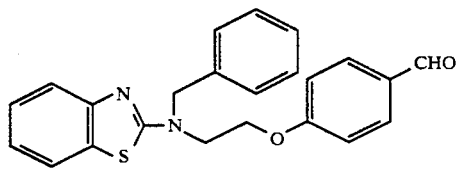

The title compound was prepared from 2-(N-(2-benzothiazolyl)-N-benzylamino)ethanol (8.25 g) and 4-fluorobenzaldehyde (3.6 g) by an analogous procedure to that described in Preparation 22.

¹H NMR δ (CDCl₃)
4.0 (2h, t); 4.4 (2H, t); 4.9 (2H, s); 6.9-8.0 (13H, complex); 10.0 (1H, s).

Preparation 31

4-[3-(N-Methyl-N-(2-benzoxazolyl)-amino)propoxy]-benzaldehyde

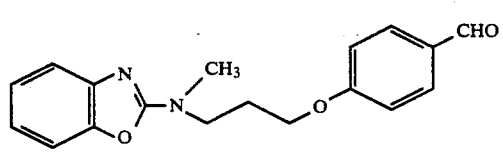

The title compound was prepared from 3-[(N-(2-benzoxazolyl)-N-methyl)amino]propan-1-ol (7.5 g) and 4-fluorobenzaldehyde (6.78 g) by a similar procedure to that described in Preparation 22.

¹H NMR δ (CDCl₃) 2.0-2.4 (2H, complex); 3.2 (3H, s); 3.75 (2H, t); 4.2 (2H, t); 6.8-7.5 (6H, complex); 7.8 (2H, d); 9.9 (1H, s).

Preparation 32

3-[(N-(2-Benzoxazolyl)-N-methyl)amino]propan-1-ol

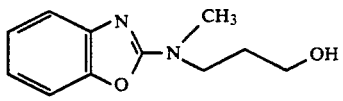

2-Chlorobenzoxazole (15.36 g) in dry tetrahydrofuran (50 ml) was added dropwise to a mixture of 3-N-methylaminopropan-1-ol (9.8 g) and triethylamine (20.2 g) in dry tetrahydrofuran (130 ml) with stirring, at room temperature. After stirring at room temperature overnight the solvent was evaporated. The residue was dissolved in dichloromethane (150 ml), washed with water (3×100 ml), brine (150 ml), dried (MgSO₄), filtered and evaporated. The title compound was obtained as an oil following chromatography on silica-gel in 2.5-3% methanol in dichloromethane.

¹H NMR δ (CDCl₃) 1.8-2.1 (2H, complex); 3.2 (3H, s); 3.5-3.85 (4H, complex); 4.3 (1H, broad s, exchanges with D₂O); 6.8-7.5 (4H, complex).

Preparation 33

4-[2-(N-Methyl-N-(2-pyridyl)amino)ethoxy]benzaldehyde

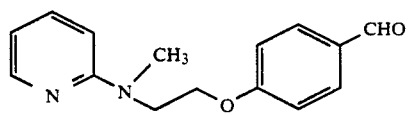

The title compound was prepared from 2-(N-methyl-N-(2-pyridyl)amino)ethanol (8.9 g) and 4-fluorobenzaldehyde by a similar procedure to that described in Preparation 22.

¹H NMR δ (CDCl₃) 3.2 (3H, s); 3.8 (2H, t); 4.2 (2H, t); 6.4 (2H, t); 6.9 (2H, d); 7.3 (1H, complex); 7.75 (2H,d); 8.15 (1H, d); 9.9 (1H, s).

Preparation 34

4-[N-(2-Benzoxazoyl)-N-methylamino]butan-1-ol

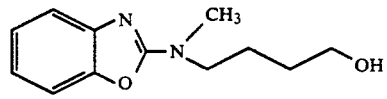

2-Chlorobenzoxazole (15.35 g) was added dropwise over 10 minutes to a stirred solution of 4-(N-methylamino)butan-1-ol (10.3 g) and triethylamine (20.3 g) in dry tetrahydrofuran (150 ml). The mixture was stirred at room temperature overnight, and then heated at reflux for a further 2h. The resulting mixture was cooled and the solvent was evaporated. The residue was dissolved in dichloromethane (500 ml), washed with saturated sodium bicarbonate solution (3×300 ml) and brine (500 ml), dried and evaporated to afford the title compound as an oil.

¹H NMR δ (DCDl₃) 1.5-2.0 (4H, complex); 3.1 (3H,s); 3.4-3.9 (5H, complex; reduced to 4H after D₂O exchange); 6.9-7.4 (4H, complex)

Preparation 35

4-[(N-(2-Benzoxazolyl)-N-methyl)amino]butan-1-ol methanesulphonyl ester

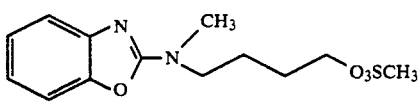

Methanesulphonyl chloride (3.15 g) was added dropwise to a stirred, ice-cooled solution of 4-[N-(2-benzoxazolyl)-N-methylamino]butan-1-ol (5.5 g) and 4-dimethylaminopyridine (0.15 g) in pyridine (100 ml). The mixture was allowed to warm to room temperature overnight, and then diluted with water (500 ml), and extracted with dichloromethane (3×200 ml).

The combined extracts were washed with saturated sodium bicarbonate solution (3×200 ml), and brine (200 ml), then dried and the solvent evaporated to afford an oil. More of this oil was obtained from the acidic aqueous layers by means of adjusting the pH to 4.5 with solid potassium carbonate, re-extracting with dichloromethane (3×200 ml), and drying and evaporating these dichloromethane layers. The combined impure product fractions were chromatographed on silica gel with 2% methanol in dichloromethane as eluent to afford the title compound as an oil.

$^1$H NMR δ (CDCl$_3$) 1.80(4H,complex); 3.05(3H,s); 3.25(3H,s); 3.60(2H,complex); 4.30(2H,complex); 6.90–7.40(4H, complex).

Preparation 36

4-[4-(N-Methyl-N-(2-benzoxazolyl)amino)butoxy]benzaldehyde

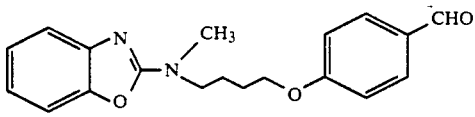

The title compound was prepared from 4-hydroxybenzaldehyde (1.71 g) and 4-[N-(2-benzoxazolyl)-N-methylamino]butan-1-ol methanesulphonyl ester (3.80 g) by a similar procedure to that used in Preparation 26.

$^1$H NMR δ (CDCl$_3$)
1.70–1.95(4H, complex); 3.20(3H,s); 3.55(2H, complex); 4.00(2H, complex); 6.80–7.40(6H, complex) 7.75(2H,d); 9.90(1H,s)

Preparation 37

2-[N-(2-Benzoxazolyl)amino]ethanol

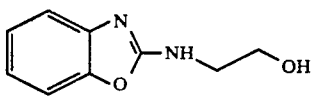

A solution of 2-chlorobenzoxazole (12.78 g) in dry tetrahydrofuran (50 ml) was added, over 10 minutes, to a stirred, ice-cooled solution of ethanolamine (15.3 g) in dry tetrahydrofuran (400 ml). The mixture was heated at reflux overnight, cooled, and the solvent evaporated. The residue was partitioned between water (500 ml) and dichloromethane (500 ml), and the resulting white solid filtered off, washed with dichloromethane and dried in vacuo to afford the title compound m.p. 162°–4° C.

$^1$H NMR δ DMSO-d$_6$ 3.3–3.8 (4H, complex); 5.0 (1H, br, exchanges with D$_2$O); 6.9–7.7 (4H, complex); 8.1 (1H, br, exchanges with D$_2$O).

Preparation 38

2-[N-(2-Benzoxazolyl)amino]ethanol methanesulphonyl ester

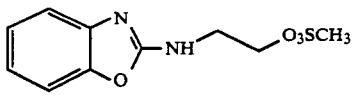

Methanesulphonyl chloride (4.9 g) was added dropwise to a stirred, ice-cooled solution of 2-[N-(2-benzoxazolyl)amino]ethanol (6.23 g) and triethylamine 4.39 g) in dichloromethane (75 ml). The resulting mixture was stirred at 0° C. for 1.5 h and then diluted with dichloromethane (200 ml), washed with water (2×200 ml), brine (200 ml) and dried. The dichloromethane layer was evaporated and the residue chromatographed on silica gel with 1.5% methanol in dichloromethane as eluent to give the title compound, m.p. 96°–9° C.

$^1$H NMR δ CDCl$_3$ 3.0 (3H,s); 3.85 (2H,t); 4.5 (2H,t); 5.9 (1H,br, exchanges with D$_2$O); 7.0–7.5 (4H, complex).

Preparation 39

4-[2-(N-(2-Benzoxazolyl)amino)ethoxy]benzaldehyde

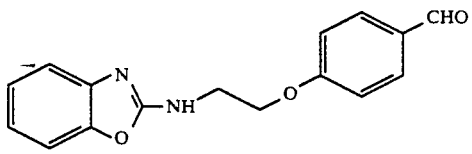

A mechanically stirred mixture of 2-[N-(2-benzoxazolyl)amino]ethanol methanesulphonyl ester (5.77 g), 4-hydroxybenzaldehyde (2.81 g) and potassium carbonate (3.28 g) was heated at 80° C. overnight in dry DMF (250 ml). After cooling, the reaction mixture was concentrated in vacuo, diluted with water (500 ml) and extracted with ethyl acetate (3×300 ml). The combined ethyl acetate layers were washed with water (2×1l), brine (1l), dried and evaporated. The resulting solid was chromatographed on silica gel with 1.5% methanol in dichloromethane as eluent to afford the title compound, m.p. 103°–6° C.

$^1$H NMR δ CDCl$_3$ 3.9 (2H,t); 4.3 (2H,t); 6.4 (1H, br, exchanges with D$_2$O); 6.9–8.0 (8H, complex); 9.9 (1H,s).

Preparation 40

2-[N-Isopropyl-N-(2-benzoxazolyl)amino]ethanol

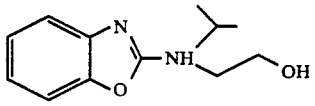

2-Chlorobenzoxazole (23.04 g) was added dropwise to an ice-cooled solution of 2-(isopropylamino)ethanol (15.45 g) and triethylamine (30.3 g) in tetrahydrofuran (500 ml). The mixture was stirred at room temperature for 30 minutes, then heated at reflux overnight before being cooled and evaporated. The residue was dissolved in dichloromethane (800 ml) and washed with saturated sodium bicarbonate solution (500 ml), water (3×1l) brine (1l), dried (MgSO₄), filtered and evaporated. The title compound was obtained as an oil following chromatography on silica gel using 1.5% methanol-dichloromethane as solvent.

¹H NMR δ (CDCl₃)

1.25 (6H,d); 3.6 (2H,t); 3.9 (2H,t); 4.5 (1H,m); 4.55 (1H, broad s, exchanges with D₂O); 6.95-7.50 (4H, complex).

Preparation 41

2-[N-Isopropyl-N-(2-benzoxazolyl)amino]ethanol methanesulphonyl ester

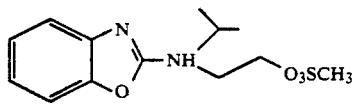

The title compound was prepared from 2-[N-isopropyl -N-(2-benzoxazolyl)amino]ethanol and methanesulphonyl chloride by a similar procedure to that described in Preparation 38.

¹H NMR δ (CDCl₃) 1.35 (6H,d); 3.0 (3H,s); 3.8 (2H,t); 4.3-4.7 (3H, complex); 6.9-7.5 (4H, complex).

Example 1

5-(4-[2-(N-Methyl-N-(2-benzothiazolyl)amino)ethoxy]-benzyl)-2,4-thiazolidinedione.

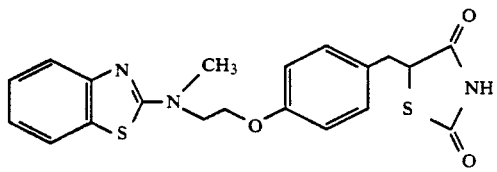

5-(4-[2-(N-Methyl-N-(2-benzothiazolyl)amino)ethoxy] benzylidene)-2,4-thiazolidinedione (2 g) in dry 1,4-dioxan (70 ml) was reduced under hydrogen in the presence of 10% palladium on charcoal (3 g) at ambient temperature and atmospheric pressure until hydrogen uptake ceased. The solution was filtered through diatomaceous earth, the filter pad was washed exhaustively with dioxan and the combined filtrates were evaporated to dryness under vacuum. The title compound (m.p. 167°-8° C.) was obtained after crystallisation from methanol.

¹H NMR δ (DMSO-d₆)

2.9-3.4 (2H, complex); 3.25 (3H, s); 3.9 (2H, complex); 4.25 (2H, complex); 4.8 (1H, complex); 6.8-7.75 (8H, complex); 12.0 (1H, s, exchanges with D₂O).

Example 2

5-(4-[2-(N-Methyl-N-(2-benzothiazolyl)amino)ethoxy] benzylidene)-2,4-thiazolidinedione

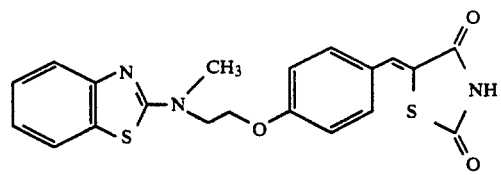

A solution of 4-[2-(N-methyl-N-(2-benzothiazolyl)amino) ethoxy]benzaldehyde (1.9 g) and 2,4-thiazolidinedione (0.8 g) in toluene (100 ml) containing a catalytic quantity of piperidinium acetate was boiled under reflux in a Dean and Stark apparatus for 2 hours. The mixture was cooled and filtered and the filtered solid was dried to give the title compound (mp 219° C.).

¹H NMR δ (DMSO - d₆) 3.2 (3H, s); 3.9 (2H, t); 4.35 (2H, t); 6.8-7.7 (10H, complex).

Example 3

5-(4-[2-(N-Methyl-N-(2-benzoxazolyl)amino)ethoxy] benzyl)-2,4-thiazolidinedione hemihydrate

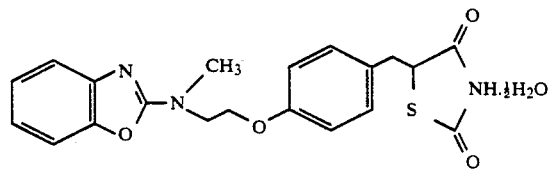

5-(4-[2-(N-Methyl-N-(2-benzoxazolyl)amino)ethoxy]-benzylidene)-2,4-thiazolidinedione (1.5 g) in dry 1,4-dioxan (80 ml) was reduced under hydrogen in the presence of 10% palladium on charcoal (2 g) at ambient temperature and atmospheric pressure until hydrogen uptake ceased. The solution was filtered through diatomaceous earth, the filter pad was washed exhaustively with dioxan and the combined filtrates were evaporated to dryness under vacuum. The title compound (mp 147°-9° C.) was obtained after crystallisation from methanol.

¹H NMR δ (DMSO-d₆+D₂O) 3.1-3.5 (2H, complex); 3.3 (3H,s); 3.95 (2H, complex); 4.25 (2H, complex); 4.5 (1H, complex); 6.8-7.3 (8H, complex).

Example 4

5-(4-(N-Methyl-N-(2-benzoxazolyl)amino)ethoxy] benzylidene)-2,4-thiazolidinedione

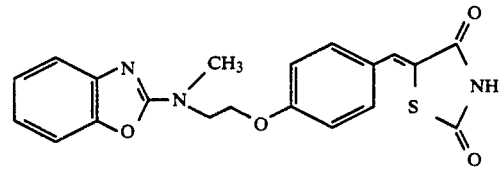

A solution of 4-[2-(N-methyl-N-(2-benzoxazolyl)amino) ethoxy]benzaldehyde (1.6 g) and 2,4-thiazolidinedione (0.63 g) in toluene (100 ml) containing a catalytic quantity of piperidinium acetate was boiled under reflux in a Dean and Stark apparatus for 2 hours. The mixture was cooled and filtered to give the title compound (mp 227°-9° C.).

¹H NMR δ (DMSO-d₆)
3.20 (3H, s); 3.90 (2H, t); 4.30 (2H, t); 6.9-7.75 (10H, complex).

Example 5

5-(4-[2-(N-Methyl-N-(2-pyrimidinyl)amino)ethoxy]benzyl)-2,4-thiazolidinedione

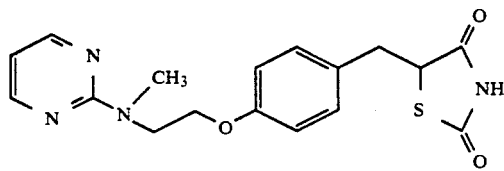

5-(4-[2-(N-Methyl-N-(2-pyrimidinyl)amino) ethoxy]benzylidene)-2,4-thiazolidinedione (2.4 g) in dry 1,4-dioxan (150 ml) was reduced under hydrogen in the presence of 10% palladium on charcoal (3 g) until hydrogen uptake ceased. The solution was filtered through diatomaceous earth, the filter pad was washed exhaustively with dioxan and the combined filtrates were evaporated to dryness under vacuum. The title compound (mp 150°-51° C.) was obtained after crystallisation from methanol.

¹H NMR δ (DMSO-d₆) 2.9-3.4 (2H, complex); 3.2 (3H, s); 3.9 (2H, complex); 4.2 (2H, complex); 4.9 (1H, complex); 6.6 (1H, t); 6.9 (2H, d); 7.2 (2H, d); 8.4 (2H, d); 12.0 (1H, broad s, exchanges with D₂O).

Example 6

5-(4-[2-(N-Methyl-N-(2-pyrimidinyl)amino)ethoxy]benzylidene)-2,4-thiazolidinedione

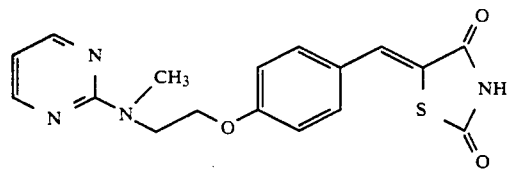

A solution of 4-[2-(N-methyl-N-(2-pyrimidinyl)amino) ethoxy]benzaldehyde (1.7 g) and 2,4-thiazolidinedione (0.7 g) in toluene (100 ml) containing a catalytic quantity of piperidinium acetate was boiled under reflux in a Dean and Stark apparatus for 2 hours. The mixture was cooled and filtered to give the title compound (mp 189°-90° C.).

¹H NMR δ (DMSO-d₆ + D₂O)
3.2 (3H, s); 3.7-4.4 (4H, complex); 6.6 (1H, t); 7.1 (2H, d), 7.5 (2H, d); 7.7 (1H, s); 8.4 (2H, d).

Example 7

5-(4-(2-(N-Methyl-N-[2-(4,5-dimethylthiazolyl)]amino)ethoxy]benzyl)-2,4-thiazolidinedione

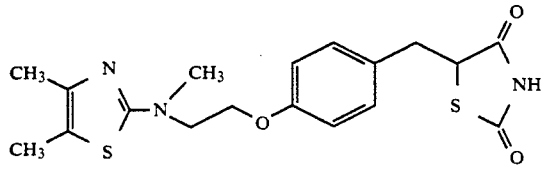

5-(4-[2-(N-Methyl-N-[2-(4,5-dimethylthiazolyl)]amino) ethoxy]benzylidene-2,4-thiazolidinedione (1.6 g) was dissolved in a mixture of methanol (50 ml) and dioxan (50 ml). Magnesium turnings (1.5 g) were added and the solution stirred until no more effervescence was observed. The mixture was added to water (300 ml), acidified (2M HCl) to form a solution, neutralised (saturated NaHCO₃ solution), filtered and dried. The solid was dissolved in dioxan (100 ml), adsorbed onto silica (20 g) and the title compound (m.p. 177° C.; MeOH) obtained following chromatography on silica-gel in 5% dioxan in dichloromethane.

¹H NMR δ (DMSO-d₆)
2.05 (3H, s); 2.15 (3H, s); 3.0 (3H, s); 3.0-3.4 (2H, complex); 3.8 (2H, t); 4.2 (2H, t); 4.85 (1H, complex); 6.9 (2H, d); 7.1 (2H, d); 12.0 (1H, broad s exchanges with D₂O).

Example 8

5-(4-[2-(N-Methyl-N-[2-(4,5-dimethylthiazolyl)]amino) ethoxy]benzylidene)-2,4-thiazolidinedione

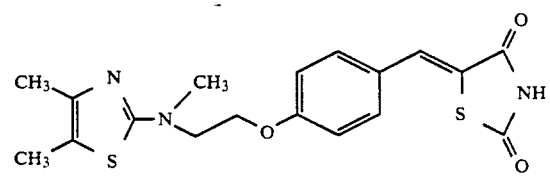

The title compound (m.p. 175° C.) was prepared by a similar procedure to that described in Example 4.

¹H NMR δ (DMSO-d₆) 2.0 (3H, s); 2.1 (3H, s); 3.0 (3H, s); 3.7 (2H, t); 4.25 (2H, t); 7.1 (2H, d); 7.55 (2H, d); 7.75 (1H, s); 12.0 (1H, broad s, exchanges with D₂O).

Example 9

5-(4-[2-(N-Methyl-N-(2-thiazolyl)amino)ethoxy]benzyl)-2,4-thiazolidinedione

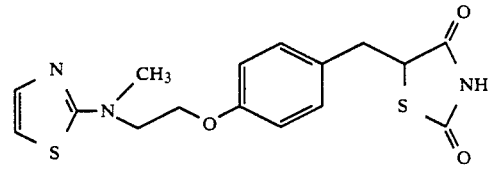

The title compound (m.p. 186° C.; MeOH) was prepared by an analogous procedure to that described in Example 7.

¹H NMR δ (DMSO-d₆) 3.0-3.4 (2H, complex); 3.1 (3H, s); 3.8 (2H, t); 4.2 (2H, t); 4.85 (1H, complex); 6.7-7.3 (6H, complex); 12.0 (1H, broad s, exchanges with D₂O).

Example 10

5-(4-[2-(N-Methyl-N-(2-thiazolyl)amino)ethoxy]benzylidene)-2,4-thiazolidinedione

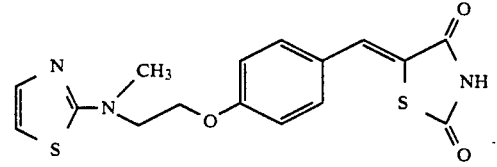

The title compound (m.p. 212° C.) was prepared by a similar procedure to that described Example 4.

¹H NMR δ (DMSO-d₆) 3.1 (3H, s); 3.85 (2H, t); 4.3(2H, t); 6.75 (1H, d); 7.1-7.3 (3H, complex); 7.6 (2H, d); 7.75 (1H, s); 12.0 (1H, broad s, exchanges with D₂O).

Example 11

5-[4-(2-(N-Methyl-N-(2-(4-phenylthiazolyl))amino) ethoxy)benzyl]-2,4-thiazolidinedione

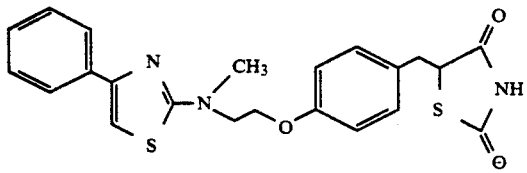

The title compound was obtained as a foam (m.p. 62°-65° C.) from 5-]4-(2-(N-methyl-N-(2-(4-phenyl-thiazolyl))amino)ethoxy)benzylidene] -2,4-thiazolidinedione (1.6 g) by a similar procedure to that described in Example 7.

¹H NMR δ (DMSO-d₆)

3.15 (3H, s); 3.0-3.4 (2H, complex); 3.9 (2H, t); 4.25 (2H, t); 4.85 (1H complex); 6.9 (2H, d); 7.1-7.45 (6H, complex); 7.85 (2H, d); 12.0 (1H, broad s, exchanges with D₂O).

Example 12

5-[4-(2-(N-Methyl-N-(2-(4-phenylthiazolyl))amino) ethoxy]benzylidene)-2,4-thiazolidinedione

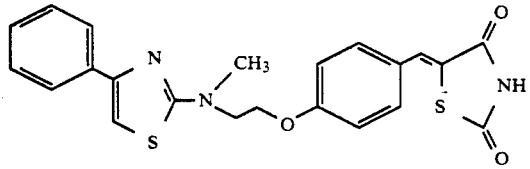

The title compound (m.p. 134° C.) was prepared from 4-[2-(N-methyl-N-(2-(4-phenylthiazolyl)amino)ethoxy]benzaldehyde by a similar procedure to that described in Example 4

¹H NMR δ (DMSO-d₆)

3.2 (3H, s); 3.9 (2H, t); 4.35 (2H, t); 7.1-7.95 (11H, complex); 12.0 (1H broad s, exchanges with D₂O).

Example 13

5-(4-[2-(N-Methyl-N-[2-(4-phenyl-5-methylthiazolyl)] amino)ethoxy]benzyl)-2,4-thiazolidinedione

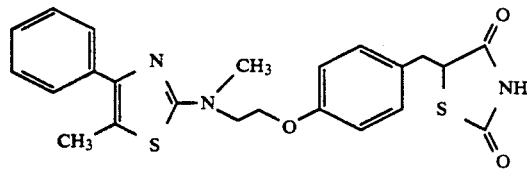

The title compound, obtained as a foam (m.p. 60°-62° C.), was prepared by an analogous procedure to that described in Example 7.

¹H NMR δ (DMSO-d₆) 2.35 (3H, s); 3.1 (3H, s); 3.0-3.4 (2H, complex); 3.8 (2H, t); 4.2 (2H, t); 4.85 (1H, complex); 6.9 (2H, d); 7.2 (2H, d); 7.25-7.5 (3H, complex); 7.65 (2H, d); 12.0 (1H, broad s, exchanges with D₂O).

Example 14

5-(4-[2-(N-Methyl-N-[2-(4-phenyl-5-methylthiazolyl)] amino)ethoxy]benzylidene)-2,4-thiazolidinedione

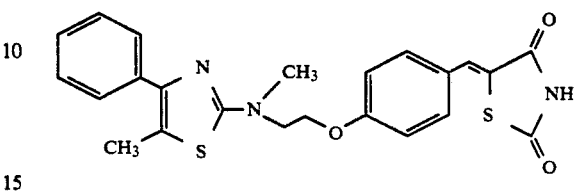

The title compound was prepared from 4-[2-(N-methyl-N-[2-(4-phenyl-5-methylthiazolyl)]amino)ethoxy] benzaldehyde by a similar procedure to that described in Example 4, and was used in Example 13 without further purification.

¹H NMR δ (DMSO-d₆)

2.4 (3H, s); 3.1 (3H, s); 3.8 (2H, t); 4.35 (2H, t); 7.1-7.75 (10H, complex); 12.0 (1H, broad s, exchanges with D₂O).

Example 15

5-(4-[2-(N-Methyl-N-[2-(4-methyl-5-phenylthiazolyl)] amino)ethoxy]benzylidene)-2,4-thiazolidinedione

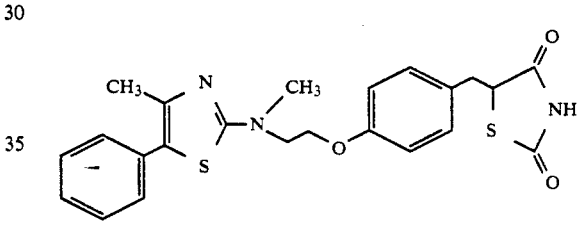

The title compound (m.p. 174° C.; MeOH) was prepared from 5-(4-[2-(N-methyl-N-2-(4-methyl-5-phenyl-thiazolyl)]-amino)ethoxy]benzylidene)2,4-thiazolidinedione by an analogous procedure to that described in Example 7.

¹H NMR δ (DMSO-d₆)

2.3 (3H, s); 3.0-3.4 (2H, complex); 3.15 (3H, s); 3.85 (2H, t); 4.25 (2H, t); 4.85 (1H, complex); 6.95 (2H, d); 7.2 (2H, d); 7.45 (5H, complex); 12.0 (1H, broad s, exchanges with D₂O).

Example 16

5-(4-[2-(N-Methyl-N-[2-(4-methyl-5-phenylthiazolyl)] amino)ethoxy]benzylidene)-2,4-thiazolidinedione

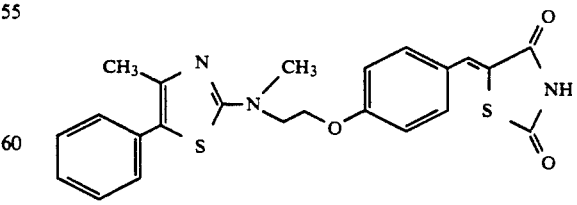

The title compound was prepared from 4-[2-(N-methyl-N-[2-(4-methyl-5-phenylthiazolyl)] amino)ethoxy]-benzaldehyde by a similar procedure to that described in Example 4, and was used in Example 15 without further purification.

¹H NMR δ (DMSO-d₆)
2.3 (3H, s); 3.1 (3H, s); 3.85 (2H, t); 4.35 (2H, t); 7.15–7.75 (10H, complex); 12.0 (1H, broad s, exchanges with D₂O).

Example 17

5-(4-[2-(N-Methyl-N-[2-(4-methylthiazolyl)]amino)ethoxy]benzyl)-2,4-thiazolidinedione

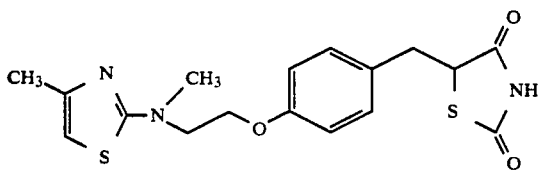

The title compound, was prepared from 5-(4-[2-(N-methyl-N-[2-(4-methylthiazolyl)]amino)ethoxy]benzylidene)-2,4-thiazolidinedione as a foam (m.p. 121° C.), by a similar procedure to that described in Example 7.

¹H NMR δ (DMSO-d₆)
2.1 (3H, s); 3.0–3.4 (2H, complex); 3.1 (3H, s); 3.75 (2H, t); 4.15 (2H, t); 4.85 (1H, complex); 6.3 (1H, s); 6.9 (2H, d); 7.2 (2H, d); 12.0 (1H, broad s, exchanges with D₂O).

Example 18

5-(4-[2-(N-Methyl-N-[2-(4-methylthiazolyl)]amino)ethoxy]benzylidene)-2,4-thiazolidinedione

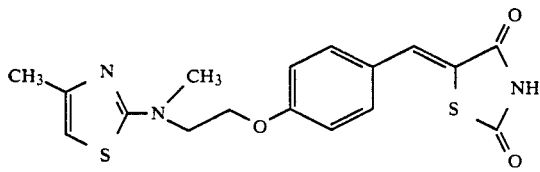

The title compound was prepared from 5-(4-[2-(N-methyl-N-[2-(4-methylthiazolyl)]amino)ethoxy]benzaldehyde by a similar procedure to that described in Example 4, and was used in the Example 17 without further purification.

¹H NMR δ (DMSO-d₆)
2.1 (3H, s); 3.1 (3H, s); 3.85 (2H, d); 4.3 (2H, d); 6.3 (1H, s); 7.15 (2H, d); 7.6 (2H, d); 7.75 (1H, s); 12.0 (1H, broad s, exchanges with D₂O).

Example 19

5-(4-[2-(N-Methyl-N-[2-(5-phenyloxazolyl)]amino)ethoxy]benzyl]-2,4-thiazolidinedione

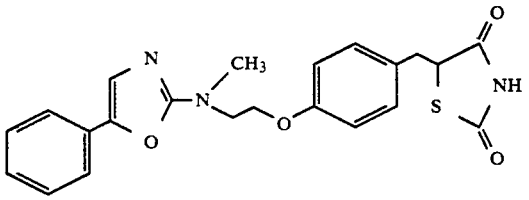

The title compound (m.p. 200° C., MeOH)) was prepared from 5-[4-(2-(N-methyl-N-[2-(5-phenyloxazolyl)-]amino ethoxy)benzylidene]-2,4-thiazolidinedione by a similar procedure to that described in Example 7.

¹H NMR δ (DMSO-d₆)
3.0–3.4 (2H, complex); 3.15 (3H, s); 3.8 (2H, t): 4.2 (2H, t): 4.85 (1H, complex); 6.9 (2H, d); 7.1–7.4 (6H, complex); 7.5 (2H, d); 12.0 (1H, broad s, exchanges with D₂O).

Example 20

5-(4-[2-(N-Methyl-N-[2-(5-phenyloxazolyl)]amino)ethoxy]benzylidene]-2,4-thiazolidinedione

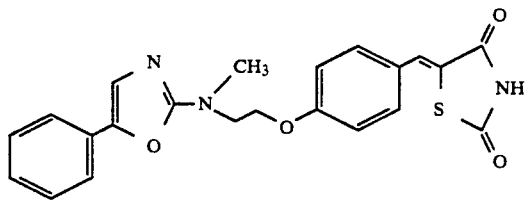

The title compound (m.p. 191° C.) was prepared from 4-[2-(N-methyl-N-[2-(5-phenyloxazolyl)]amino) ethoxy]benzaldehyde by an analogous procedure to that described in Example 4.

¹H NMR δ (DMSO-d₆)
3.2 (3H, s); 3.8 (2H, t); 4.35 (2H, t); 7.1–7.7 10H, complex); 7.8 (1H, s); 12.0 (1H, broad s, exchanges with D₂O).

Example 21

5-(4-[2-(N-Methyl-N-[2-(4,5-dimethyloxazolyl)]amino)ethoxy]benzyl)-2,4-thiazolidinedione

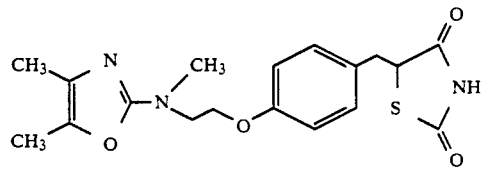

5-(4-[2-(N-Methyl-N-[2-(4,5-dimethyloxazolyl)-]amino-ethoxy] benzylidene)-2,4-thiazolidinedione (1.2 g) in dry 1,4-dioxan (100 ml) was reduced under hydrogen in the presence of 10% Palladium on charcoal (2.5 g) until hydrogen uptake ceased. The solution was filtered through diatomaceous earth, the filter pad was washed exhaustively with dioxan and the combined filtrates evaporated to dryness under vacuum. The title compound was obtained as a foam (m.p. 53°–54° C.) following chromatography on silica-gel in 1% methanol in dichloromethane.

¹H NMR δ (DMSO-d₆)
1.85 (3H, s); 2.05 (3H, s); 3.0 (3H, s); 3.0–3.4 (2H, complex); 3.65 (2H, t); 4.1 (2H, t); 4.85 (1H, complex); 6.85 (2H, d); 7.15 (2H, d); 12.0 (1H, broad s, exchanges with D₂O).

Example 22

5-(4-[2-(N-Methyl-N-[2-(4,5-dimethyloxazolyl)]amino)ethoxy]benzylidene)-2,4-thiazolidinedione

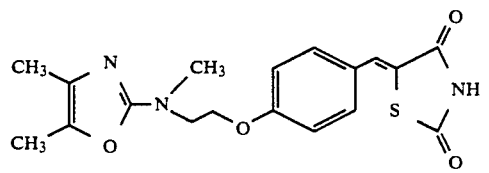

The title compound (softens at 149° C.) was prepared by a similar procedure to that described in Example 4.

¹H NMR δ (DMSO-d₆)
1.85 (3H, s); 2.05 (3H, s); 3.0 (3H, s); 3.7 (2H, t); 4.25 (2H, t); 7.1 (2H, d); 7.5 (2H, d); 7.75 (1H, s); 12.0 (1H, broad s, exchanges with D₂O).

Example 23

5-[4-(2-(2-Pyrimidinylamino)ethoxy)benzyl]-2,4-thiazolidinedione

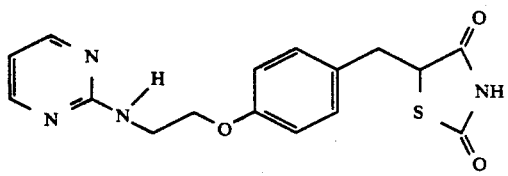

A mixture of 5-[4-(2-(2-pyrimidinylamino)ethoxy)benzylidene]-2,4-thiazolidinedione (3 g) and 10% palladium on charcoal (9 g) in DMF (70 ml) was stirred under a pressure of 200 psi of hydrogen until hydrogen uptake ceased. The mixture was filtered through diatomaceous earth, and the filter pad washed exhaustively with DMF. The combined filtrates were evaporated to dryness and the title compound (m.p. 173° C.) obtained following recrystallization from methanol.

¹H NMR δ (DMSO-d₆)
3.0–3.4 (2H, complex); 3.65 (2H, complex); 4.1 (2H, t); 4.85 (1H, complex); 6.6 (1H, t); 6.85 (2H, d); 7.15 (2H, d); 7.25 (1H, t, exchanges with D₂O); 8.3 (2H, d); 12.0 (1H, broad s, exchanges with D₂O).

Example 24

5-[4-(2-(2-Pyrimidinylamino)ethoxy)benzylidene]-2,4-thiazolidinedione

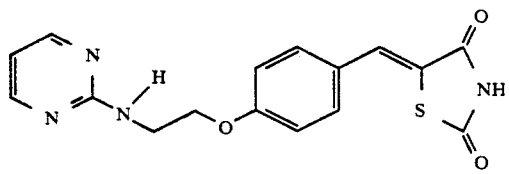

The title compound (m.p. 234° C.) was obtained from 4-[2-(2-pyrimidinylamino)ethoxy]benzaldehyde and 2,4-thiazolidindione, by an analogous procedure to that described in Example 6.

¹H NMR δ (DMSO-d₆)
3.65 (2H, complex); 4.2 (2H,t); 6.6 (1H, t); 7.2–7.6 (5H, complex, one proton changes with D₂O); 7.7 (1H, s); 8.3 (2H, d); 12.0 (1H, broad s, exchanges with D₂O).

Example 25

5-(4-[2-(N-Acetyl-N-(2-pyrimidinyl)amino)ethoxy]benzyl)-2,4-thiazolidinedione

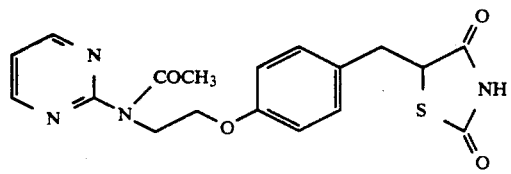

A stirred solution of 5-[4-(2-(2-pyrimidinylamino)ethoxy)benzyl]-2,4-thiazolidinedione (800 mg) in acetic anhydride (15 ml) and 1,4-dioxan (5 ml) was boiled under reflux for 3 hours. After cooling, the mixture was added to water (300 ml), neutralized (sodium bicarbonate) and extracted with dichloromethane (3×200 ml). The organic extracts were washed with brine (100 ml), dried (MgSO₄), filtered and evaporated to dryness. Chromatography on silica-gel in dichloromethane of the residual oil afforded the title compound (m.p. 137° C.).

¹H NMR δ (DMSO-d₆) 2.3 (3H, s); 2.93.4 (2H, complex); 4.15 (2H,t); 4.35 (2H, t); 4.85 (1H, complex); 6.7 (2H,d); 7.1 (2H, d); 7.35 (1H, t); 8.8 (2H, d); 12.0 (1H, broad s, exchanges with D₂O).

Example 26

5-(4-(2-(N-(2-Benzothiazolyl)-N-benzylamino)ethoxy)benzylidene)-2,4-thiazolidinedione

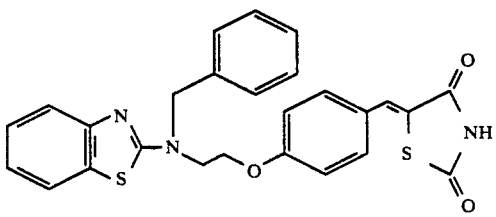

4-(2-(N-(2-Benzothiazolyl)-N-benzylamino)ethoxy)benzaldehyde (3 g) and 2,4-thiazolidinedione (1 g) were dissolved in toluene (200 ml) containing piperidine (0.2 ml) and benzoic acid (0.2 g) and heated to reflux for 4h. in a Dean and Stark apparatus. On cooling, the solution was concentrated under vacuum to 50% of its volume and the title compound, which crystallised, was collected by filtration and dried in vacuo (m.p. 185°–188° C.). It was used in Example 27 without further purification.

¹H NMR δ (DMSO-d₆)
4.0 (2H, t); 4.4 (2H, t); 4.9 (2H, s); 7.1–7.9 (14H, complex); 12–13 (1H, broad s, exchanges with D₂O).

Example 27

5-(4-(2-(N-(2-Benzothiazolyl)-N-benzylamino)ethoxy)benzyl)-2,4-thiazolidinedione

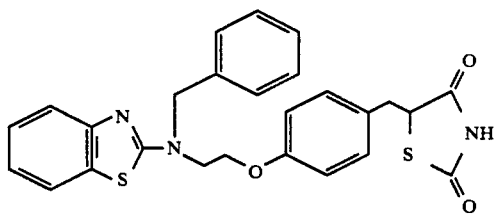

5-(4-(2-(N-(2-Benzothiazolyl)-N-benzylamino)ethoxy) benzylidene)-2,4-thiazolidinedione (2.4 g) in dioxan (150 ml) was hydrogenated in the presence of 10% palladium-charcoal (4.8 g) for 3h. at room temperature and atmospheric pressure. A further portion of catalyst (2.4 g) was added and the hydrogenation continued for a total of 20h. The mixture was filtered through diatomaceous earth and the solvent was evaporated. The residue was chromatographed on silica gel with 3% methanol-dichloromethane as eluant to afford the title compound as a foam, which collapsed at 78° C.

¹H NMR δ (CDCl₃) 3.1 (1H, dd); 3.4 (1H, dd); 4.0 (2H, t); 4.25 (2H, t); 4.5 (1H, dd); 4.9 (2H, s); 6.8–7.6 (13H, m); 8.3 (1H, broad s, exchanges with D₂O).

Example 28

5-(4-[3-(N-Methyl-N-(2-benzoxazolyl)amino)propoxy]benzyl)-2,4-thiazolidinedione

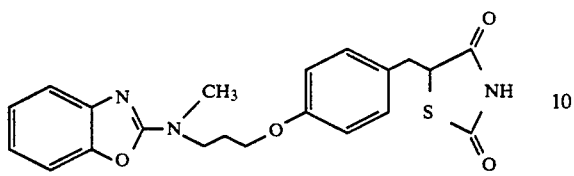

The title compound (m.p. 171°-3° C.; ethanol) was prepared from 5-(4-[3-(N-methyl-N-(2-benzoxazolyl)amino)-propoxy]benzylidene)-2-4-thiazolidinedione by a similar procedure to that described in Example 1.

$^1$H NMR δ (DMSO - d$_6$) 2.0-2.35 (2H, complex); 2.9-3.6 (2H, complex); 3.2 (3H, s); 3.7 (2H, t); 4.2 (2H, t); 4.9 (1H, complex); 6.8-7.4 (8H, complex); 12-12.5 (1H, broad s, exchanges with D$_2$O).

Example 29

5-(4-[3-(N-Methyl-N-(2-benzoxazolyl)amino)propoxy]benzylidene)-2,4-thiazolidinedione

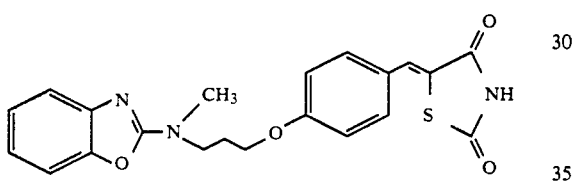

The title compound (m.p. 202°-204° C.) was prepared from 4-[3-(N-methyl-N-(2-benzoxazolyl)amino)propoxy]benzaldehyde (5.3 g) and 2,4-thiazolidinedione (2,2 g) by a similar procedure to that described in Example 4.

$^1$H NMR δ (DMSO - d$_6$)

2.0-2.35 (2H, complex); 3.15 (3H, s); 3.7 (2H, t); 4.2 (2H, t); 7.0-7.7 (8H, complex); 7.8 (1H, s); 12.0 (1H, broad s, exchanges with D$_2$O).

Example 30

5-(4-[2-(N-Methyl-N-(2-pyridyl)amino)ethoxy]benzyl)-2,4-thiazolidinedione

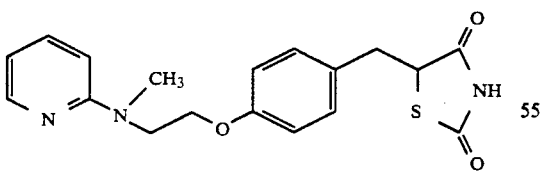

The title compound (m.p. 153°-5° C.; MeOH) was obtained from 5-(4-[2-(N-methyl-N-(2-pyridyl)amino)ethoxy]-benzylidene)-2,4-thiazolidinedione by a similar procedure to that described in Example 1.

$^1$H NMR δ (DMSO - d$_6$)

2.9-3.4 (2H, complex); 3.1 (3H, s); 3.9 (2H, t); 4.15 (2H, t); 4.8 (1H, complex); 6.5-6.85 (2H, complex); 6.8 (2H, d); 7.2 (2H, d); 7.5 (1H, complex); 8.1 (1H, d); 12.05 (1H, broad s, exchanges with D$_2$O).

Example 31

5-(4-[2-(N-Methyl-N-(2-pyridyl)amino)ethoxy]benzylidene)-2,4-thiazolidinedione

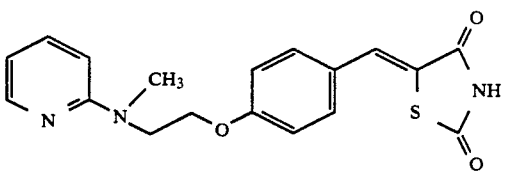

The title compound (m.p. 177°-9° C.) was obtained from 4-[2-(N-methyl-N-(2-pyridyl)amino)ethoxy]benzaldehyde (3.2 g) and 2,4-thiazolidinedione (1.1 g) by a similar procedure to that described in Example 4.

$^1$H NMR δ (DMSO-D$_2$O)

3.1 (3H, s); 3.9 (2H, t); 4.2 (2H, t); 6.4-7.5 (7H, complex); 7.7 (1H, s); 8.1 (1H, d)

Example 32

5-(4-[4-(N-Methyl-N-(2-benzoxazolyl)amino)ethoxy]benzylidene)-2,4-thiazolidinedione

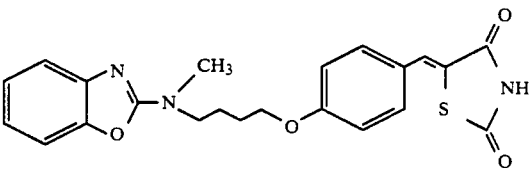

The title compound (m.p. 168° C.) was prepared from 4-[4-(N-methyl-N-(2-benzoxazolyl)amino)butoxy]benzaldehyde (3.5 g) and 2,4-thiazolidinedione (1.4 g) by a similar procedure to that described in Example 4.

$^1$H NMR δ DMSO-d$_6$ 1.70 (4H, complex); 3.10 (3H, s); 3.25 (1H, exchanges with D$_2$O); 3.50 (2H, complex); 4.05 (2H, complex); 6.90-7.60 (8H, complex); 7.70 (1H, s).

Example 33

5-(4-[4-(N-Methyl-N-(2-benzoxazolyl)amino)ethoxy]benzyl)-2,4-thiazolidinedione

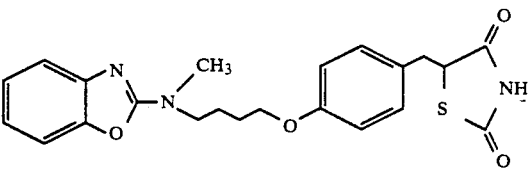

The title compound (m.p. 112° C., ethanol-hexane) was prepared from 5-(4-[4-(N-methyl-N-(2-benzoxazolyl)amino)butoxy]benzylidene)-2,4-thiazolidinedione by a similar procedure to that described in Example 1.

$^1$H NMR δ CDCl$_3$ 1.85 (4H, complex); 3.10 (1H, complex); 3.15 (3H,s); 3.40 (1H,dd); 3.60 (2H,t); 4.00 (2H,t); 4.50 (1H,dd); 6.80-7.40 (8H, complex); 9.30 (1H, br, exchanges with D$_2$O).

Example 34

5-(4-[2-(N-(2-Benzoxazolyl)amino)ethoxy]-benzylidene)-2,4-thiazolidinedione

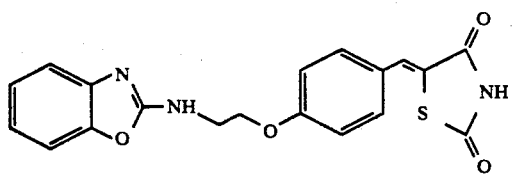

The title compound (m.p. 242°-5° C.) was prepared from 4-[2-(N-(2-benzoxazolyl)amino)ethoxy]benzaldehyde (5.18 g) and 2,4-thiazolidinedione (2.36 g) by a similar procedure to that described in Example 4.

$^1$H NMR δ DMSO-d$_6$ 3.80 (2H,t); 4.35 (2H,t); 7.00-8.00 (9H, complex); 8.20 (1H, br, exchanges with D$_2$O); 13.5 (1H, br, exchanges with D$_2$O).

Example 35

5-(4-[2-(N-(2-Benzoxazolyl)amino)ethoxy]-benzyl)-2,4-thiazolidinedione

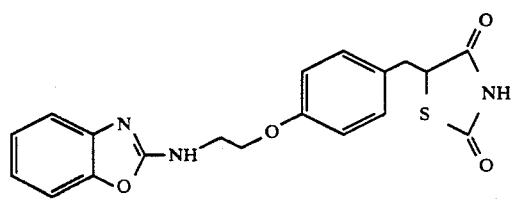

The title compound (m.p. 202°-3° C.; dichloromethane) was prepared from 5-(4-[2-N-(2-benzoxazolyl)amino)ethoxy] benzylidene)-2,4-thiazolidinedione (6.1 g) by a similar procedure to that described in Example 1.

$^1$H NMR δ DMSO-d$_6$ 3.10 (1H,dd); 3.30 (1H,ddd) 3.70 (2H, complex); 4.15 (2H,t); 4.85 (1H,dd); 6.80-7.50 (8H, complex); 8.15 (1H, complex; exchanges with D$_2$O); 12.00 (1H, br, exchanges with D$_2$O).

Example 36

5-(4-[2-(N-Isopropyl-N-(2-benzoxazolyl)amino)ethoxy] benzyl)-2,4-thiazolidinedione

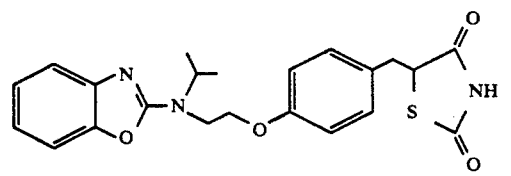

Sodium hydride (60% dispersion in mineral oil, 0.93 g) was added portionwise to a stirred solution of 5-(4-hydroxybenzyl)-2,4-thiazolidinedione (2.45 g in dry DMF (50 ml)) at room temperature under a nitrogen atmosphere. The mixture was stirred for 1 hour prior to the addition of a solution of 2-[N-isopropyl-N-(2-benzoxazolyl)amino]ethanol methanesulphonyl ester (3.3 g) in dry DMF (60 ml). After stirring at room temperature for a further hour, the mixture was heated at 80° C. for 21 hours, then cooled, diluted with water (1 l) and acidified to pH 6.5 with hydrochloric acid. The resulting suspension was extracted with ethyl acetate (2×500 ml), and the combined ethyl acetate layers washed with water (3×1 l), brine (1 l), dried (MgSO$_4$) and evaporated. The residual oil was chromatographed on silica gel with 1.5% methanol-dichloromethane as solvent to afford the title compound as a foam (m.p. 66° C.).

$^1$H NMR δ (CDCl$_3$)

1.35 (6H,d); 3.1 (1H, dd); 3.4 (1H, dd); 3.8 (2H,t); 4.15 (2H, complex); 4.35-4.65 (2H, complex); 6.85-7.4 (8H, complex); and 9.15 (12H, broad s,; exchanges with D$_2$O).

DEMONSTRATION OF EFFICACY OF COMPOUNDS

Obese Mice, Oral Glucose Tolerance Test

C57bl/6 obese (ob/ob) mice were fed on powdered oxoid diet. After at least one week, the mice continued on a powdered oxoid diet or were fed powdered oxoid diet containing the test compound. After 8 days on the supplemented diet all of the mice were fasted for 5 hours prior to receiving an oral load of glucose (3 g/kg). Blood samples for glucose analysis were taken 0, 45, 90 and 135 minutes after glucose administration and the results appear below as the percentage reduction in area under the blood glucose curve where test compound treated groups are compared with the control groups. 7 mice were used for each treatment.

| EXAMPLE NO: | LEVEL IN DIET (μmol kg$^{-1}$ of DIET) | % REDUCTION IN AREA UNDER BLOOD GLUCOSE CURVE |
|---|---|---|
| 1 | 100 | 51 |
| 2 | 300 | 30 |
| 3 | 10 | 39 |
| 4 | 300 | 30 |
| 5 | 100 | 40 |
| 7 | 50 | 47 |
| 9 | 100 | 58 |
| 11 | 100 | 34 |
| 13 | 100 | 37 |
| 15 | 100 | 39 |
| 17 | 100 | 34 |
| 19 | 30 | 22 |
| 21 | 30 | 33 |
| 24 | 30 | 15 |
| 25 | 30 | 19 |
| 27 | 300 | 56 |
| 29 | 300 | 32 |
| 33 | 300 | 25 |
| 35 | 100 | 44 |
| 36 | 100 | 20 |

Anti-Hypertensive Activity

Eight month old female, spontaneously hypertensive rats were given test compound once each day for 15 days. Prior to the experiment and on days 8 and 15, the rats were fasted overnight from 5.00 pm and blood pressure was recorded the following morning, immediately prior to dosing and again 2h later. Food was returned after the 2h blood pressure reading.

The results below were obtained using the compound of Example 3 as the test compound.

| Treatment Group | Time | Blood pressure (mm Hg) | |
|---|---|---|---|
|  |  | 0 hours | 2 hours |
| Control | Day 0 | 210 ± 13 | — |
| Test Compound (30 μmole/kg) | Day 0 | 210 ± 13 | — |

| Treatment Group | Time | Blood pressure (mm Hg) 0 hours | 2 hours |
|---|---|---|---|
| Test Compound (10 μmole/kg) | Day 0 | 210 ± 13 | — |
| Control | Day 8 | 196 ± 11 | 195 ± 12 |
| Test Compound (30 μmole/kg) | Day 8 | 181 ± 11* | 174 ± 15** |
| Test Compound (10 μmole/kg) | Day 8 | 191 ± 6 | 185 ± 12 |
| Control | Day 15 | 208 ± 12 | 208 ± 9 |
| Test Compound (30 μmole/kg) | Day 15 | 178 ± 18** | 170 ± 13*** |
| Test Compound (10 μmole/kg) | Day 15 | 198 ± 17 | 185 ± 5*** |

Significance of difference from control value at same timepoint: *p < 0.05; p < 0.01; *p < 0.001.

Toxicology

No toxicological effects were indicated for any of the compounds of the invention in any of the abovementioned tests.

I claim:

1. A compound of formula (III):

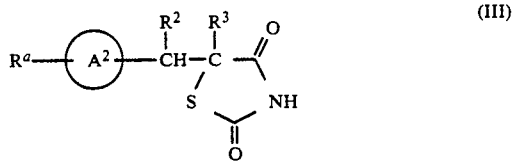

wherein $R^2$, $R^3$, $A^2$ and $R^8$ are defined as follows:

$R^2$ and $R^3$ may each represent hydrogen or $R^2$ and $R^3$ together represent a bond;

$A^2$ represents a benzene ring having three optional substituents which may be selected from halogen, substituted or unsubstituted $C_{1-12}$-alkyl or $C_{1-12}$-alkoxy; substituents for the alkyl group being selected from the groups consisting of halogen, $C_{1-12}$-alkyl, phenyl, $C_{1-12}$-alkoxy halo-$C_{1-12}$-alkyl, hydroxy, amino, nitro, carboxy, $C_{1-12}$-alkoxycarbonyl, $C_{1-12}$-alkoxycarbonyl-$C_{1-12}$-alkyl, $C_{1-12}$-alkylcarbonyloxy, or $C_{1-12}$-alkylcarbonyl;

and wherein $R^8$ is fluorine or $R^8$ is a moiety of formula $R^1HN(CH_2)_nO$, wherein $R^1$, and n are as defined as follows:

$R^1$ represents a hydrogen atom, a $C_{1-12}$-alkyl group, a $C_{1-6}$ alkylcarbonyl group, an aryl-$C_{1-12}$-alkyl group, the aryl moiety being substituted or unsubstituted or a substituted or unsubstituted aryl group;

any aryl group being phenyl or naphthyl optionally substituted with up to five groups selected from halogen, $C_{1-12}$-alkyl, phenyl, $C_{1-12}$-alkoxy, halo-$C_{1-12}$-alkyl, hydroxy, amino, nitro, carboxy, $C_{1-12}$-alkylcarbonyloxy, or a $C_{1-12}$-alkylcarbonyl group; and n represents an integer in the range of from 2 to 6.

* * * * *

UNITED STATES PATENT AND TRADEMARK OFFICE
CERTIFICATE OF CORRECTION

PATENT NO. : 5,260,445
DATED : November 9, 1993
INVENTOR(S) : Richard Mark Hindley It is certified that error appears in the above-identified patent and that said Letters Patent is hereby corrected as shown below:

Claim 1, column 40, line 9, "$R^8$" should be --$R^a$-- as shown in formula recited in claim 1.

line 18, insert a comma (,) after "-alkoxy";

line 22, $R^8$ (double occurrence) should be --$R^a$--.

Signed and Sealed this

Nineteenth Day of April, 1994

*Attest:*

BRUCE LEHMAN

*Attesting Officer*     *Commissioner of Patents and Trademarks*